(12) United States Patent
Cheng et al.

(10) Patent No.: US 12,109,353 B2
(45) Date of Patent: Oct. 8, 2024

(54) DYNAMIC PRESSURE RESPONSE AND CATHETER OCCLUSION SYSTEM

(71) Applicant: C. R. Bard, Inc., Franklin Lakes, NJ (US)

(72) Inventors: Jason Jishen Cheng, Avondale Estates, GA (US); David M. Simiele, Roswell, GA (US); Varad Chavan, Kolhapur (IN)

(73) Assignee: C. R. Bard, Inc., Franklin Lakes, NJ (US)

( * ) Notice: Subject to any disclaimer, the term of this patent is extended or adjusted under 35 U.S.C. 154(b) by 8 days.

(21) Appl. No.: 17/542,060

(22) Filed: Dec. 3, 2021

(65) Prior Publication Data
US 2022/0176031 A1   Jun. 9, 2022

Related U.S. Application Data

(60) Provisional application No. 63/128,687, filed on Dec. 21, 2020, provisional application No. 63/121,774, filed on Dec. 4, 2020.

(51) Int. Cl.
*A61M 1/00* (2006.01)
*A61M 25/00* (2006.01)

(52) U.S. Cl.
CPC ............... *A61M 1/84* (2021.05); *A61M 1/69* (2021.05); *A61M 25/0017* (2013.01); *A61M 2205/33* (2013.01)

(58) Field of Classification Search
CPC ........ A61M 1/0023; A61M 1/63; A61M 1/69; A61M 1/71; A61M 1/73; A61M 1/83;
(Continued)

(56) References Cited

U.S. PATENT DOCUMENTS 3,114,916 A   12/1963   Hadley
3,583,401 A   6/1971   Vailiancourt et al.
(Continued)

FOREIGN PATENT DOCUMENTS

EP   1872752 A1   1/2008
EP   2417955 A2   2/2012
(Continued)

OTHER PUBLICATIONS

PCT/US2022/049418 filed Nov. 9, 2022 International Search Report and Written Opinion dated Feb. 10, 2023.
(Continued)

*Primary Examiner* — Leslie A Lopez
*Assistant Examiner* — Jihad Dakkak
(74) *Attorney, Agent, or Firm* — Rutan & Tucker LLP

(57) ABSTRACT

Embodiments disclosed herein are directed to a dynamic response drainage and occlusion system configured to drain a fluid from a patient. The drainage system includes an input airflow device to provide airflow into the drainage lumen, a pressure sensor to measure pressure within the drainage tube, and an output airflow device to provide airflow out of the drainage tube. A controller including control logic configured to acquire pressure data from the pressure sensor, determine a running pressure rate-of-change from the acquired pressure data, compare the running pressure rate-of-change with a pressure rate-of-change defined by the control logic, and adjust an operating characteristic of at least one of the input airflow device and the output airflow device to move the running pressure rate-of-change toward the pressure rate-of-change defined by the control logic. The system further includes catheter occlusions systems to automatically protect the patient from pressure spikes within the system.

19 Claims, 14 Drawing Sheets

(58) Field of Classification Search
CPC .. A61M 1/84; A61M 1/94; A61M 2025/0001; A61M 2025/0002; A61M 2025/0018; A61M 2202/0496; A61M 2205/33; A61M 2205/3331; A61M 2205/3334; A61M 2205/3344; A61M 2205/3351; A61M 2205/3355; A61M 2205/3379; A61M 2205/50; A61M 2206/20; A61M 2210/1078; A61M 2210/1085; A61M 25/0017; A61M 1/74; A61B 5/7203; A61B 5/7239; A61B 5/6852

See application file for complete search history.

(56) References Cited

U.S. PATENT DOCUMENTS

| | | |
|---|---|---|
| 3,598,124 A | 8/1971 | Andersen et al. |
| 3,661,143 A | 5/1972 | Henkin |
| 3,861,394 A | 1/1975 | Villari |
| 3,901,235 A | 8/1975 | Patel et al. |
| 3,955,574 A | 5/1976 | Rubinstein |
| 4,084,593 A | 4/1978 | Jarund |
| 4,265,243 A | 5/1981 | Taylor |
| 4,305,403 A | 12/1981 | Dunn |
| 4,315,506 A | 2/1982 | Kayser et al. |
| 4,360,933 A | 11/1982 | Kimura et al. |
| 4,465,485 A | 8/1984 | Kashmer et al. |
| 4,531,939 A | 7/1985 | Izumi |
| 4,631,061 A | 12/1986 | Martin |
| 4,654,029 A | 3/1987 | D'Antonio |
| 4,747,166 A | 5/1988 | Kuntz |
| 4,819,684 A | 4/1989 | Zaugg et al. |
| 4,872,579 A | 10/1989 | Palmer |
| 4,990,137 A | 2/1991 | Graham |
| 5,002,528 A | 3/1991 | Palestrant |
| 5,071,411 A | 12/1991 | Hillstead |
| 5,186,431 A | 2/1993 | Tamari |
| 5,318,550 A | 6/1994 | Cermak et al. |
| 5,405,319 A * | 4/1995 | Abell ................ A61M 3/0208 604/27 |
| 5,738,656 A | 4/1998 | Wagner et al. |
| 5,813,842 A | 9/1998 | Tamari |
| 5,894,608 A | 4/1999 | Birbara |
| 6,007,521 A | 12/1999 | Bidwell et al. |
| 6,106,506 A * | 8/2000 | Abell ....................... F16K 7/07 604/257 |
| 6,183,454 B1 | 2/2001 | Levine et al. |
| 8,266,741 B2 | 9/2012 | Penninger et al. |
| 8,337,475 B2 | 12/2012 | Christensen et al. |
| 8,475,419 B2 | 7/2013 | Eckermann |
| 8,512,301 B2 | 8/2013 | Ma |
| 10,391,275 B2 | 8/2019 | Burnett et al. |
| 10,426,919 B2 | 10/2019 | Erbey, II et al. |
| 10,506,965 B2 | 12/2019 | Cooper et al. |
| 10,737,057 B1 | 8/2020 | Mikhail et al. |
| 10,772,998 B2 | 9/2020 | Luxon et al. |
| 2002/0000253 A1 | 1/2002 | Fillmore et al. |
| 2002/0161317 A1 | 10/2002 | Risk et al. |
| 2003/0078638 A1 | 4/2003 | Voorhees et al. |
| 2004/0176746 A1 | 9/2004 | Forral |
| 2004/0230181 A1 | 11/2004 | Cawood |
| 2004/0236292 A1 | 11/2004 | Tazoe et al. |
| 2004/0254547 A1 | 12/2004 | Okabe et al. |
| 2005/0209585 A1 | 9/2005 | Nord et al. |
| 2005/0245898 A1 | 11/2005 | Wright et al. |
| 2005/0261619 A1 | 11/2005 | Gay |
| 2006/0015190 A1 | 1/2006 | Robertson |
| 2006/0079854 A1 | 4/2006 | Kay et al. |
| 2006/0155260 A1 | 7/2006 | Blott et al. |
| 2006/0235353 A1 | 10/2006 | Gelfand et al. |
| 2006/0270971 A1 | 11/2006 | Gelfand et al. |
| 2006/0271019 A1 | 11/2006 | Stoller et al. |
| 2007/0078444 A1* | 4/2007 | Larsson ................... A61M 1/74 604/540 |
| 2007/0142729 A1 | 6/2007 | Pfeiffer et al. |
| 2007/0272311 A1 | 11/2007 | Trocki et al. |
| 2008/0156092 A1 | 7/2008 | Boiarski |
| 2009/0157016 A1 | 6/2009 | Adahan |
| 2009/0157040 A1 | 6/2009 | Jacobson et al. |
| 2009/0326483 A1 | 12/2009 | Green |
| 2010/0106116 A1 | 4/2010 | Simmons et al. |
| 2010/0130949 A1 | 5/2010 | Garcia |
| 2011/0060300 A1 | 3/2011 | Weig et al. |
| 2012/0036638 A1 | 2/2012 | Penninger et al. |
| 2012/0323144 A1* | 12/2012 | Coston .................. A61M 1/82 600/581 |
| 2013/0218106 A1* | 8/2013 | Coston .................. A61M 1/00 604/317 |
| 2014/0200558 A1 | 7/2014 | McDaniel |
| 2015/0126975 A1 | 5/2015 | Wuthier |
| 2015/0290448 A1 | 10/2015 | Pavlik |
| 2016/0135982 A1 | 5/2016 | Garcia |
| 2016/0183819 A1 | 6/2016 | Burnett et al. |
| 2016/0310711 A1 | 10/2016 | Luxon et al. |
| 2017/0072125 A1 | 3/2017 | Wallenås et al. |
| 2017/0136209 A1 | 5/2017 | Burnett et al. |
| 2017/0143566 A1 | 5/2017 | Elku et al. |
| 2017/0241978 A1 | 8/2017 | Duval |
| 2017/0312114 A1 | 11/2017 | Glithero |
| 2018/0015251 A1 | 1/2018 | Lampotang et al. |
| 2018/0071441 A1 | 3/2018 | Croteau et al. |
| 2018/0104391 A1 | 4/2018 | Luxon et al. |
| 2018/0110456 A1* | 4/2018 | Cooper .................. A61B 5/205 |
| 2018/0125697 A1 | 5/2018 | Ferrera |
| 2018/0177458 A1 | 6/2018 | Burnett et al. |
| 2018/0235523 A1 | 8/2018 | Sauder |
| 2018/0245699 A1 | 8/2018 | Lee |
| 2018/0360424 A1 | 12/2018 | Yurek et al. |
| 2019/0009021 A1 | 1/2019 | Nelson et al. |
| 2019/0009023 A1 | 1/2019 | Diperna et al. |
| 2019/0038451 A1 | 2/2019 | Harvie |
| 2019/0046102 A1 | 2/2019 | Kushnir et al. |
| 2019/0126006 A1 | 5/2019 | Rehm et al. |
| 2019/0143094 A1 | 5/2019 | DeMeritt |
| 2019/0151610 A1 | 5/2019 | Fletter |
| 2019/0343445 A1* | 11/2019 | Burnett .................. A61B 5/207 |
| 2020/0000979 A1 | 1/2020 | Myers |
| 2020/0061281 A1* | 2/2020 | Desouza ............. A61M 1/1601 |
| 2020/0315837 A1 | 10/2020 | Radl et al. |
| 2021/0077007 A1 | 3/2021 | Jouret et al. |
| 2022/0152345 A1 | 5/2022 | Simiele et al. |
| 2022/0160949 A1 | 5/2022 | Simiele et al. |
| 2022/0193366 A1 | 6/2022 | Cheng et al. |
| 2022/0218890 A1 | 7/2022 | Chavan |
| 2022/0218973 A1 | 7/2022 | Chavan et al. |
| 2022/0218974 A1 | 7/2022 | Chavan et al. |
| 2022/0273213 A1 | 9/2022 | Sokolov et al. |
| 2022/0305189 A1 | 9/2022 | Chavan et al. |
| 2022/0330867 A1 | 10/2022 | Conley et al. |
| 2022/0362080 A1 | 11/2022 | McCorquodale et al. |
| 2022/0409421 A1 | 12/2022 | Hughett et al. |
| 2023/0013353 A1 | 1/2023 | Chavan et al. |
| 2023/0030637 A1 | 2/2023 | Gloeckner et al. |
| 2023/0054937 A1 | 2/2023 | Chancy et al. |
| 2023/0083906 A1 | 3/2023 | Jones et al. |
| 2023/0310837 A1 | 10/2023 | Gamsizlar et al. |
| 2024/0238500 A1 | 7/2024 | Simiele et al. |

FOREIGN PATENT DOCUMENTS

| | | |
|---|---|---|
| EP | 2730299 A1 | 5/2014 |
| WO | 2009/026237 A1 | 2/2009 |
| WO | 2012016179 A1 | 2/2012 |
| WO | 2015019056 A1 | 2/2015 |
| WO | 2015/105916 A1 | 7/2015 |
| WO | 2016012494 A1 | 1/2016 |
| WO | 2017177068 A1 | 10/2017 |
| WO | 2018136306 A1 | 7/2018 |
| WO | 2018191193 A1 | 10/2018 |
| WO | 2019004854 A1 | 1/2019 |
| WO | 2020033752 A1 | 2/2020 |
| WO | 2021154427 A1 | 8/2021 |

(56) References Cited

FOREIGN PATENT DOCUMENTS

| | | |
|---|---|---|
| WO | 2022/159333 A1 | 7/2022 |
| WO | 2022/251425 A1 | 12/2022 |
| WO | 2023086394 A1 | 5/2023 |

OTHER PUBLICATIONS

U.S. Appl. No. 17/526,994, filed Nov. 15, 2021 Restriction Requirement dated Jan. 3, 2023.
U.S. Appl. No. 17/556,942, filed Dec. 20, 2021 Non-Final Office Action dated Jan. 31, 2023.
U.S. Appl. No. 17/561,504, filed Dec. 23, 2021 Non-Final Office Action dated Mar. 14, 2023.
PCT/US2020/066707 filed Dec. 22, 2020 International Search Report and Written Opinion dated Apr. 15, 2021.
PCT/US2022/012373 filed Jan. 13, 2022 International Search Report and Written Opinion dated Apr. 19, 2022.
U.S. Appl. No. 17/526,994, filed Nov. 15, 2021 Non-Final Office Action dated May 10, 2023.
U.S. Appl. No. 17/532,454, filed Nov. 22, 2021 Non-Final Office Action dated Mar. 22, 2023.
U.S. Appl. No. 17/561,458, filed Dec. 23, 2021 Non-Final Office Action dated Jun. 16, 2023.
U.S. Appl. No. 17/902,705, filed Sep. 2, 2022 Non-Final Office Action dated May 24, 2023.
U.S. Appl. No. 17/556,942, filed Dec. 20, 2021 Advisory Action dated Sep. 1, 2023.
U.S. Appl. No. 17/556,942, filed Dec. 20, 2021 Final Office Action dated Jul. 12, 2023.
U.S. Appl. No. 17/561,458, filed Dec. 23, 2021 Final Office Action dated Sep. 12, 2023.
U.S. Appl. No. 17/561,504, filed Dec. 23, 2021 Final Office Action dated Jul. 19, 2023.
U.S. Appl. No. 17/863,898, filed Jul. 13, 2022 Non-Final Office Action dated Jul. 17, 2023.
U.S. Appl. No. 17/902,705, filed Sep. 2, 2022 Final Office Action dated Aug. 17, 2023.
U.S. Appl. No. 17/373,568, filed Jul. 12, 2021 Non-Final Office Action dated Nov. 9, 2023.
U.S. Appl. No. 17/526,994, filed Nov. 15, 2021 Advisory Action dated Jan. 19, 2024.
U.S. Appl. No. 17/526,994, filed Nov. 15, 2021 Final Office Action dated Oct. 24, 2023.
U.S. Appl. No. 17/532,454, filed Nov. 22, 2021 Final Office Action dated Sep. 27, 2023.
U.S. Appl. No. 17/532,454, filed Nov. 22, 2021 Notice of Allowance dated Dec. 8, 2023.
U.S. Appl. No. 17/556,942, filed Dec. 20, 2021 Non-Final Office Action dated Nov. 3, 2023.
U.S. Appl. No. 17/561,458, filed Dec. 23, 2021 Notice of Allowance dated Dec. 6, 2023.
U.S. Appl. No. 17/561,504, filed Dec. 23, 2021 Non-Final Office Action dated Nov. 27, 2023.
U.S. Appl. No. 17/561,504, filed Dec. 23, 2021 Notice of Allowance dated Jan. 22, 2024.
U.S. Appl. No. 17/863,898, filed Jul. 13, 2022 Advisory Action dated Jan. 30, 2024.
U.S. Appl. No. 17/863,898, filed Jul. 13, 2022 Final Office Action dated Nov. 22, 2023.
U.S. Appl. No. 17/902,705, filed Sep. 2, 2022 Advisory Action dated Oct. 19, 2023.
U.S. Appl. No. 17/902,705, filed Sep. 2, 2022 Non-Final Office Action dated Dec. 7, 2023.
U.S. Appl. No. 17/373,568, filed Jul. 12, 2021 Notice of Allowance dated Apr. 26, 2024.
U.S. Appl. No. 17/526,994, filed Nov. 15, 2021 Non-Final Office Action dated Apr. 22, 2024.
U.S. Appl. No. 17/556,942, filed Dec. 20, 2021 Final Office Action dated Apr. 4, 2024.
U.S. Appl. No. 17/796,604, filed Jul. 29, 2022 Notice of Allowance dated May 1, 2024.
U.S. Appl. No. 17/863,898, filed Jul. 13, 2022 Non-Final Office Action dated Mar. 11, 2024.
U.S. Appl. No. 17/902,705, filed Sep. 2, 2022 Final Office Action dated May 22, 2024.
U.S. Appl. No. 17/556,942, filed Dec. 20, 2021 Notice of Allowance dated Jun. 26, 2024.

* cited by examiner

DYNAMIC PRESSURE RESPONSE AND CATHETER OCCLUSION SYSTEM

PRIORITY

This application claims the benefit of priority to U.S. Patent Application No. 63/121,774, filed Dec. 4, 2020, and to U.S. Patent Application No. 63/128,687, filed Dec. 21, 2020, each of which is incorporated by reference in its entirety into this application.

SUMMARY

Briefly summarized, embodiments disclosed herein are directed to dynamic pressure response systems and catheter occlusion systems for automated clearing of drainage fluid from dependent loops of a fluid drainage system.

Passive fluid drainage systems can experience dependent loops where slack portions of drainage tubing create positive inclines and trap fluid within the tube. This stagnant fluid collects within the drainage tube and can affect accurate measurement of fluid output, as well as posing an infection risk and an increased potential for fluid reflux into the patient, among other complications. For example, urine pooling within a drainage tube can become a source of catheter associated urinary tract infection ("CAUTI") causing agents such as bacteria, microbes, and the like. Hospital Acquired Infections ("HAI"), such as CAUTI, are detrimental to the patient, and also incur extra costs in treating these additional complications.

Active clearing of dependent loops can use a pressure differential to push stagnant fluid downstream, into a fluid collection container. These active clearing systems can produce a large pressure differential which can be detrimental to the patient and to the collection equipment. Embodiments disclosed herein are directed to automatic clearing of these dependent loops while mitigating damage to the collection system and trauma to the patient. Embodiments can further include catheter occlusion systems configured to protect the patient from these pressure differentials. The catheter occlusion systems can be coupled to, or removed from, existing catheter/fluid drainage systems, which are already placed within a patient. The catheter occlusion system can compress a portion of the elastic catheter or drainage tube, to occlude the lumen without causing permanent deformation to the lumen. Further the catheter occlusion system can use pneumatic or hydraulic pressure to compress the catheter, allowing for the system to be coupled to, and synchronized with, positive pressure lumen clearing systems. Embodiments also include a catheter occlusion system included with a stabilization system.

Disclosed herein is a drainage system configured to drain a fluid from a patient. The drainage system may comprise a drainage tube defining a drainage tube lumen to provide fluid communication between a catheter and a collection container. The drainage system may further comprise an input airflow device coupled to the drainage tube to provide airflow into the drainage tube lumen, a pressure sensor operatively coupled to the drainage tube to measure an internal pressure within the drainage tube lumen, and an output airflow device coupled to the collection container to provide airflow out of drainage tube and the collection container. A controller is communicatively coupled to the pressure sensor, the input air flow device, and the output airflow device. The controller may include control logic configured to acquire pressure data from the pressure sensor, determine a running pressure rate-of-change from the acquired pressure data, compare the running pressure rate-of-change with a pressure rate-of-change defined by the control logic, and adjust an operating characteristic of at least one of the input airflow device and the output airflow device to move the running pressure rate-of-change toward the pressure rate-of-change defined by the control logic.

In some embodiments, the control logic may be configured to adjust an operating characteristic of the output airflow device to move the running pressure rate-of-change toward the predefined pressure rate-of-change. In some embodiments, the control logic may be configured to compare the running pressure rate-of-change with a positive pressure rate-of-change limit and deactivate the input airflow device when the pressure rate-of-change exceeds the positive pressure rate-of-change limit. Similarly, the control logic may be configured to compare the running pressure rate-of-change with a negative pressure rate-of-change limit and deactivate the output airflow device when the pressure rate-of-change exceeds the negative pressure rate-of-change limit.

In some embodiments, the control logic may be configured to determine an internal pressure of the drainage tube from the acquired pressure data, compare the internal pressure with a positive pressure limit defined by the control logic, and deactivate the input airflow device when the internal pressure exceeds the positive pressure limit. Similarly, the control logic may be configured to compare the internal pressure with a negative pressure limit defined by the control logic and deactivate the output airflow device when the internal pressure exceeds the negative pressure limit.

In some embodiments, the system may further comprise a valve coupled in line with the drainage tube at a location distal the input airflow device, wherein the valve is configured to selectively allow fluid flow through the valve when open and prevent fluid flow through the valve when closed. The control logic may further be configured to close the valve when at least one of the input airflow device and the output airflow device is activated. In some embodiments, the valve includes a catheter occlusion system having a body defining a channel configured to receive a portion of the catheter therein, and a first inflation chamber configured to transition between a deflated state and an inflated state, a portion of the first inflation chamber extending into the channel in the inflated state to compress the catheter and occlude the catheter lumen.

In some embodiments, the inflation chamber includes one of an expandable balloon or a piston having a piston head slidably engaged therewith. In some embodiments, the inflation chamber extends between the deflated state and the inflated state along an inflation axis that extends perpendicular to the longitudinal axis, the inflation axis being offset from a radial mid-point of the catheter lumen, disposed between a channel opening and the radial mid-point of the catheter lumen. In some embodiments, the body encircles the catheter through an arc of 360° and defines a toroidal cross-sectional shape. In some embodiments, the system further includes an inflation line coupled to the input airflow device and configured to provide an inflation fluid to the inflation chamber.

In some embodiments, the system may comprise a safety pressure sensor operatively coupled to the drainage tube at a location distal the valve and communicatively coupled to the controller. The control logic may be configured to acquire pressure data from the safety pressure sensor and determine an internal pressure of the catheter from the acquired pressure data from the safety pressure sensor. The control logic may be further configured to compare the internal pressure of the catheter with at least one of a positive pressure limit for the catheter defined by the control logic and a negative pressure limit for the catheter defined by the control logic. The control logic may be further configured to deactivate the input airflow device and the output airflow device when the internal pressure of the catheter exceeds the positive pressure limit for the catheter or the negative pressure limit for the catheter.

In some embodiments, the control logic may be configured to acquire pressure data from the pressure sensor while the input airflow device is deactivated and generate one or more pressure parameters from the pressure data. The control logic may be further configured to compare the one or more pressure parameters with one or more corresponding pressure parameter limits defined by the control logic. The control logic may activate the input airflow device when a pressure parameter exceeds at least one of the one or more corresponding pressure parameter limits.

In some embodiments, the control logic is configured to deactivate the input airflow device after a predefined activation time period defined by the control logic. In some embodiments, the system comprises a hydrophobic filter coupled in line with the drainage tube between the collection container and the output airflow device. In some embodiments, the catheter is a Foley catheter configured to drain a fluid from a bladder of a patient.

Also disclosed herein is a method of draining fluid from a patient. The method includes providing a drainage system comprising a drainage tube extending between a catheter and a collection container, wherein the drainage tube, the catheter and the collection container are in fluid communication with each other. The drainage system further comprises a pressure sensor operatively coupled to the drainage tube to measure pressure within the drainage tube, an input airflow device coupled to the drainage tube at a distal end to provide airflow into the drainage tube, a valve coupled in line with the drainage tube between the catheter and the input airflow device, wherein the valve is configured to selectively allow fluid flow through the valve when open and prevent fluid flow through the valve when closed, and an output airflow device coupled to the collection container, the output airflow device configured to draw airflow out of the collection container. The system further includes a controller coupled to the pressure sensor, the input airflow device, the output airflow device, and the valve, and the controller includes control logic.

The method further comprises acquiring pressure data from the pressure sensor, generating one or more pressure parameters from the pressure data, comparing the one or more pressure parameters with one or more corresponding pressure parameter limits; and activating the input airflow device when at least one pressure parameter exceeds at least one of the one or more corresponding pressure parameter limits. In some embodiments, at least one of the one or more corresponding pressure parameter limits is a high pressure limit or a pressure rate-of-change limit.

The method may further include closing the valve when the input airflow device is activated. The method may further include activating the output airflow device when the input airflow device is activated. In some embodiments, at least one of the one or more pressure parameters is a running pressure rate-of-change and the method further comprises modulating the airflow of at least one of the input airflow device and the output airflow device to move the running pressure rate-of-change toward a pressure rate-of-change defined by the control logic. The method may comprise deactivating the input airflow device when the running pressure rate-of-change exceeds a positive pressure rate-of-change limit defined by the control logic. Similarly, the method may comprise deactivating the output airflow device when the running pressure rate-of-change exceeds a negative pressure rate-of-change limit defined by the control logic.

In some embodiments, at least one of the one or more pressure parameters is an internal pressure of the drainage tube, and the method further comprises deactivating the input airflow device when the internal pressure exceeds a positive pressure limit defined by the control logic. In some embodiments, at least one of the one or more pressure parameters is a pressure noise, and the method further comprises increasing an airflow rate of the input airflow device when the pressure noise exceeds a high pressure noise limit defined by the control logic. Similarly, the method may further comprise deactivating the input airflow device when the pressure noise is below a low pressure noise limit defined by the control logic.

The method may comprise deactivating the input airflow source after an activation time period defined by the control logic, and the method may also comprise deactivating the output airflow device when the input airflow device is deactivated. The method may further comprise opening the valve when both the input airflow device and the output airflow device are deactivated.

Also disclosed is a catheter occlusion system for occluding a lumen of a catheter, an axial length of the catheter defining a longitudinal axis, the catheter occlusion system including, a body defining a channel configured to receive a portion of the catheter therein, and a first inflation chamber configured to transition between a deflated state and an inflated state, a portion of the first inflation chamber extending into the channel in the inflated state to compress the catheter and occlude the catheter lumen.

In some embodiments, the inflation chamber includes one of an expandable balloon or a piston having a piston head slidably engaged therewith. A surface of the balloon or a surface of the piston includes an adhesive configured to adhere to an outer surface of the catheter and secure the catheter occlusion system thereto. The body includes a rigid structure that partially surrounds the longitudinal axis of the catheter. The body defines a "horse-shoe" cross-sectional shape or "C-shaped" cross-sectional shape. In some embodiments, the catheter occlusion system further includes a second inflation chamber disposed opposite the first inflation chamber across the longitudinal axis of the catheter, the first inflation chamber and the second inflation chamber configured to compress the catheter therebetween in the inflated state. The first inflation chamber extends between the deflated state and the inflated state along an axis that extends perpendicular to the longitudinal axis. The inflation axis of the inflation chamber aligns with a radial mid-point of the catheter lumen. The inflation axis of the inflation chamber is offset from a radial mid-point of the catheter lumen, disposed between a channel opening and the radial mid-point of the catheter lumen.

In some embodiments, the body encircles the catheter through an arc of 360° and defines a toroidal cross-sectional shape. In some embodiments, a first portion of the body is releasably engaged with a second portion and includes one of a latch, clasp, hinge, or living hinge. In some embodiments, the catheter occlusion system further includes an inflation line configured to provide an inflation fluid to one of the first inflation chamber or an inlet to a drainage lumen that is in fluid communication with the catheter lumen, the inlet disposed proximally of the first inflation chamber. The inflation line simultaneously provides an inflation fluid to the first inflation chamber and the inlet. In some embodiments, the body is formed of a flexible material and encircles the longitudinal axis of the catheter through an arc of more than 360° to define the channel. A first portion of the body is coupled to a second portion of the body by one of a buckle, clasp, hook and loop attachment, or adhesive. The first inflation chamber includes an elongate balloon extending through a wall of the body, parallel to the longitudinal axis of the catheter. In some embodiments, the catheter is a Foley catheter configured to drain a fluid from a bladder of a patient.

Also disclosed is a catheter stabilization and occlusion system including, a body defining a channel configured to receive and stabilize a portion of a catheter, an anchor pad coupled to a lower surface of the body and including an adhesive layer configured to adhere the body to a skin surface of a patient, and an inflation balloon or an inflation piston configured to transition between a retracted state and an extended state to compress the catheter and occlude a catheter lumen in the extended state.

In some embodiments, the body includes a latch extending across the channel to releasably retain the catheter within the channel and inhibit movement of the catheter along one of the longitudinal, lateral, or transverse axes. In some embodiments, the inflation balloon extends perpendicular to the channel and, in the extended state, compresses the catheter against one of the body or the latch to occlude the catheter lumen. In some embodiments, the piston is disposed within the body and includes a piston head that transitions along an axis extending perpendicular to the longitudinal axis of the catheter between the retracted state and an extended state to compress the catheter against one of the body or the latch. In some embodiments the catheter stabilization and occlusion system further includes an inflation line configured to provide a positive pressure inflation fluid, to one of the inflation balloon or the piston, to transition from the retracted state to the extended state and a negative pressure inflation fluid to transition from the extended state to the retracted state. In some embodiments, the catheter is configured to drain urine from a patient.

Also disclosed is a method of clearing a fluid from a drainage lumen including, coupling a catheter occlusion system to an outer surface of the catheter, providing a positive pressure fluid to the occlusion system, compressing a portion of the catheter, occluding the catheter lumen, and providing a positive pressure fluid to the drainage lumen.

In some embodiments, the methods further includes disposing the catheter within a channel of the catheter occlusion system, the channel defined by a rigid body encircling between 180° and 360° of a longitudinal axis of the catheter. The rigid body includes a first body portion and a second body portion releasably or hingedly coupled thereto, the first body portion and the second body portion co-ordinate for define the channel. In some embodiments, the methods further includes wrapping a flexible body of the catheter occlusion system about the catheter, the body extending more that 360° about a longitudinal axis of the catheter. A first portion of the body is releasably coupled to a second portion of the body using one of a buckle, clasp, hook and loop attachment, or adhesive. In some embodiments, the methods further includes providing the positive pressure fluid to one of an inflation balloon or a piston to transition between a deflated state and an inflated state to compress the catheter. In some embodiments, the catheter is configured to drain urine from a bladder of a patient.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1:
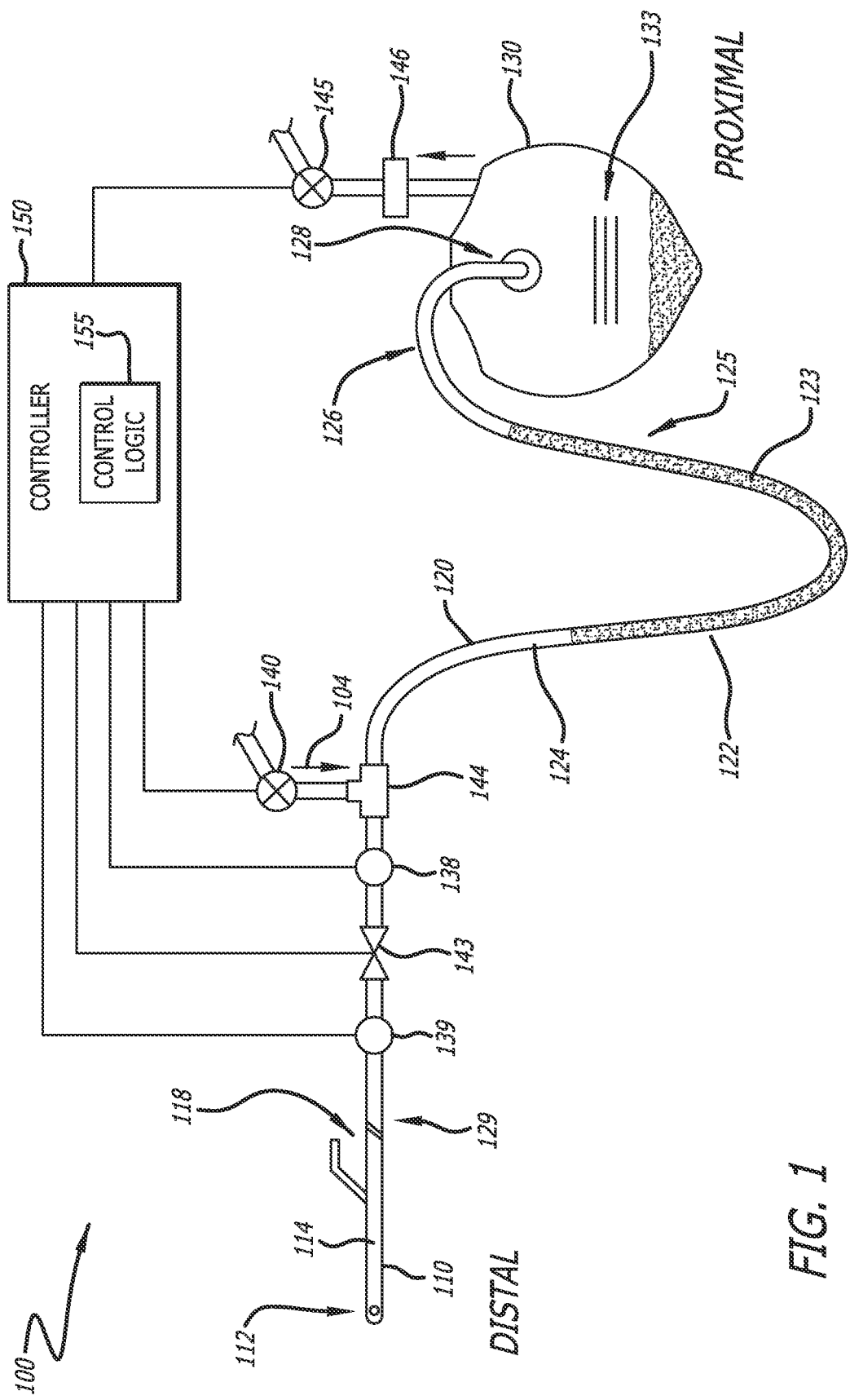
FIG. 1 shows an exemplary catheter and fluid collection system including a dynamic pressure response system, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

In the following description, the terms "or" and "and/or" as used herein are to be interpreted as inclusive or meaning any one or any combination. As an example, "A, B or C" or "A, B and/or C" mean "any of the following, A, B, C, A and B, A and C, B and C, A, B and C." An exception to this definition will occur only when a combination of elements, components, functions, steps or acts are in some way inherently mutually exclusive.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

The phrases "connected to" and "coupled to" refer to any form of interaction between two or more entities, including mechanical, electrical, magnetic, electromagnetic, fluid, signal, communicative, operative, and thermal interaction. Two components may be connected or coupled to each other even though they are not in direct contact with each other. For example, two components may be coupled to each other through an intermediate component.

The phrase "to exceed" means to go beyond. For example, a parameter may exceed an upper parameter limit by going above the upper parameter limit or exceed a lower parameter limit by going below the lower parameter limit. Similarly, a parameter may exceed a positive limit by going more positive than the positive limit or the parameter may exceed a negative limit by going more negative than the negative limit.

Figure 5:
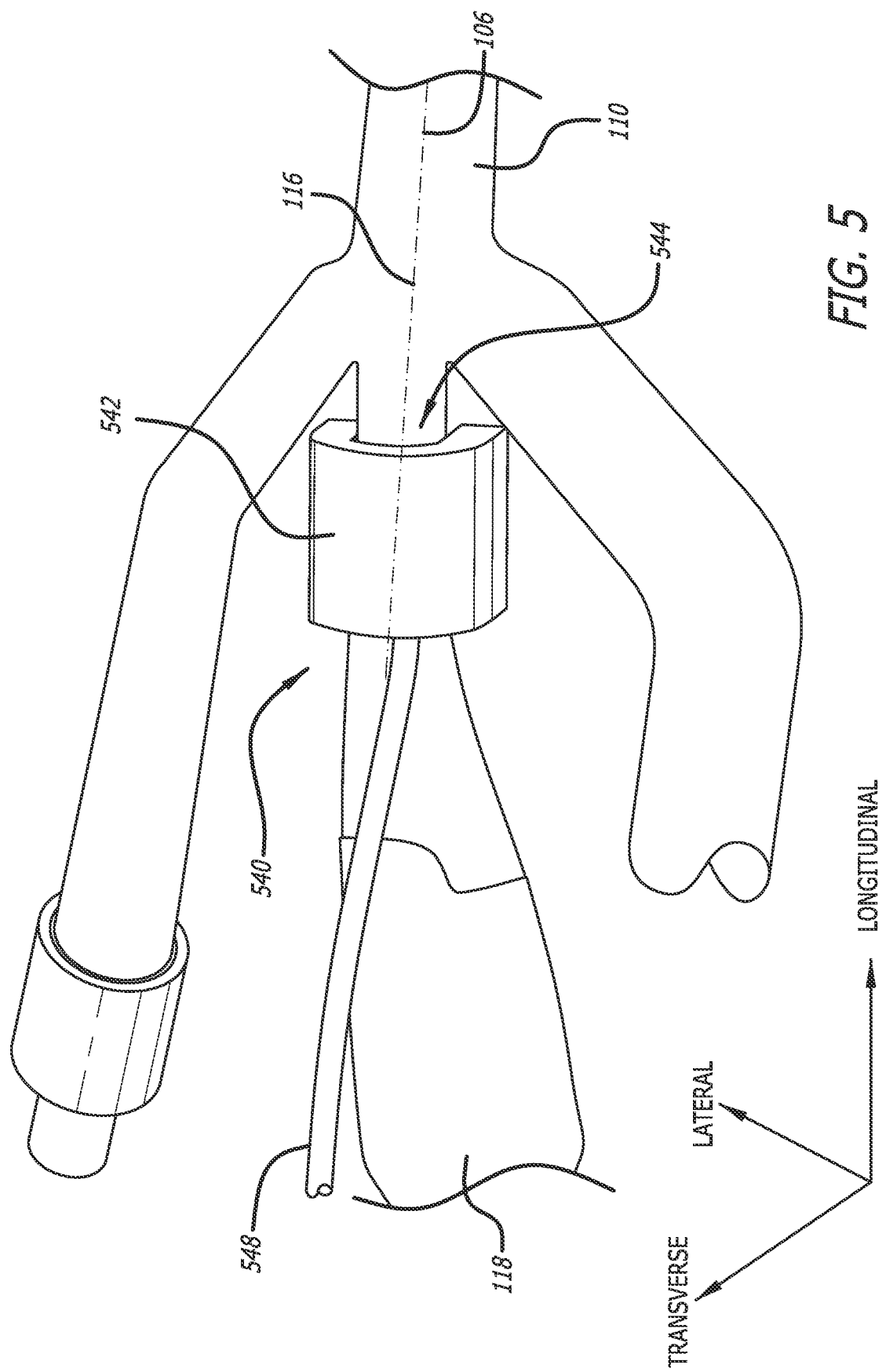
FIG. 5 shows a perspective view of a catheter occlusion system coupled with a catheter, in accordance with embodiments disclosed herein.

To assist in the description of embodiments described herein, as shown in FIG. 5, a longitudinal axis extends substantially parallel to an axial length of the catheter. A lateral axis extends normal to the longitudinal axis, and a transverse axis extends normal to both the longitudinal and lateral axes. As used herein, the term "fluid" can include any liquid or gas in a flowable state.

Unless defined otherwise, all technical and scientific terms used herein have the same meaning as commonly understood by those of ordinary skill in the art.

FIG. 1 shows an exemplary dynamic pressure response drainage system ("system") 100, which includes a catheter 110, a drainage tube 120, a collection container ("container") 130, and a controller 150. Exemplary catheters 110 include indwelling catheters, Foley catheters, balloon catheters, peritoneal drainage catheters, or the like, and are configured to be inserted into an orifice within the body of a patient to drain a fluid therefrom. Exemplary body fluids can include urine, blood, interstitial fluid, peritoneal fluid, saliva, mucus, or the like. In an embodiment, the catheter 110 can be inserted through the urethra and into a bladder of a patient. The catheter 110 includes an eyelet 112 that provides fluid communication with a lumen of the catheter 110, and is configured to drain a fluid, e.g. urine.

The drainage tube 120 extends from a distal end 129 to a proximal end 128 to define an axial length, and defines a lumen 124. The distal end 129 of the drainage tube 120 can be in fluid communication with a proximal 118 end of the catheter 110. The drainage tube 120 provides fluid communication between the lumen 114 of the catheter 110 and the collection container 130. The drainage tube 120 can be formed of rubber, plastic, polymer, silicone, a visco-elastic material, or similar suitable material. The collection container 130 can include a rigid container, a flexible collection bag, or similar suitable container for receiving a fluid, e.g. urine, drained from the catheter 110. In an embodiment, the container 130 includes a drainage outlet to allow the fluid to be emptied from the collection container 130. In an embodiment, the container 130 includes an outlet vent configured to allow air or similar gas to be released from the collection container 130. In an embodiment, the outlet vent can include a filter, valve, or similar structure configured to allow gas to escape from the container but to prevent a liquid from passing through the outlet vent.

In operation, the drainage system 100 may facilitate a passive draining process of fluid 123 from the patient without incident. In some instances, one or more complications may arise during the passive draining process requiring corrective action. As shown in FIG. 1, the flexibility of the drainage tube 120 can result in sections of the drainage tube 120 having a positive incline relative to the direction of fluid flow therethrough. Positive incline sections allow dependent loops to form, which can lead to urine pooling within the drainage tube 120. FIG. 1 shows a dependent loop 122 which may be any portion of the drainage tube 120 that is lower than a downstream portion (e.g., lower in height relative to ground) so as to create a positive incline relative to the direction of fluid flow. Dependent loops 122 can form in slack portions of the drainage tube 120. The dependent loop 122 may be a complete loop, a partial loop, or any segment of tubing 120 that causes fluid 123 to pool in the drainage tube 120. In use, one or multiple dependent loops 122 can form along the length of the drainage tube 120.

In some instances, the pooling of fluid 123 may interrupt passive drainage flow in such a way as to produce a change in internal pressure of the drainage tube 120. The change in pressure may be an increase in internal pressure of the drainage tube 120 and/or a variability of the internal pressure. In such instances, measuring and analyzing the pressure within the drainage tube 120 may provide an indication that a corrective action may be needed or desirable.

In instances of fluid pooling, a draining tube clearing process as described herein may provide a corrective action to the pooling of fluid 123. In an embodiment, an input airflow device 140, e.g. a pump or the like, can introduce an airflow and provide a positive air pressure 104 into the lumen 124 of the drainage tube 120 at a point that is distal to the dependent loop 122. The positive air pressure 104 can urge the fluid 123 through the drainage tube lumen 124 and into the container 130.

In some embodiments, the container 130 may be a soft container such as the bag shown in FIG. 1. In other embodiments, the container 130 may be a rigid container. In an embodiment, the container 130 can include a vent (not shown) configured to control an air flow in to and/or out of the container 130, and thus allow the pressure inside the container to equalize with atmospheric pressure. Worded differently, the vent may facilitate maintenance of a zero "0" (or substantially zero) gauge pressure within the container 130.

In an embodiment, the container 130 may include indicia 133 such as volumetric graduation marks to indicate a liquid volume within the container 130. If the container 130 is a bag, the bag may be configured such that the graduation marks accurately indicate liquid volume only if the pressure inside the bag is substantially equal to atmospheric pressure, i.e., zero "0" gauge pressure (or substantially zero). In other words, if the pressure within the bag is positive, the indicated liquid volume by the graduation marks may be less than the actual liquid volume in the container 130. Similarly, if the pressure within the bag is negative, the indicated liquid volume by the graduation marks may be more than the actual liquid volume in the container 130. As such, maintaining an atmospheric pressure within the container 130 may be beneficial to accurate measuring of drainage fluid volume from the patient.

In an embodiment, the system 100 may include a connector 144. The connector 144 may include an inlet configured to couple with an outlet of the catheter 110, an outlet configured to couple with the drainage tube 120 and a side port configured to couple with the input airflow device 140 (e.g., the pump).

In an embodiment, the system 100 may include a valve system ("valve") 143 disposed between the catheter 110 and the drainage tube 120. More specifically, the valve 143 may be disposed between the catheter 110 and the input airflow device 140. In an embodiment, the valve 143 can be configured to transition between a closed position and an open position. In an embodiment, the valve 143 may be configured to selectively isolate the catheter 110 from the drainage tube 120. In other words, the valve 143, when closed, may prevent an internal pressure of the drainage tube 120 from affecting a pressure within a lumen 114 of the catheter 110. Similarly, the valve 143, when closed, may prevent fluid 123 within the drainage tube 120 from flowing into the catheter lumen 114.

In an embodiment, the valve 143 may be a mechanical valve, an electro-mechanical valve, e.g., a solenoid valve, a hydraulic valve, a pneumatic valve, combinations thereof, or the like. In an embodiment, the valve 143 may be biased toward the closed position, i.e., the valve may be disposed in the closed position when deactivated and disposed in the open position when activated. In other embodiments, the valve 143 may be a normally open valve. In some embodiments, the valve 143 may be a check valve configured to allow flow in a proximal direction and prevent flow in the distal direction. In some embodiments, the valve 143 may be integral to the connector 144. In such an embodiment, the valve 143 may be disposed distally of the connector 144. In an embodiment, the valve 143 can include a catheter occlusion system as described in more detail herein.

In an embodiment, the system 100 can further include a first pressure sensor 138 coupled to the drainage tube 120 and configured to measure an internal pressure of the drainage lumen 124 at location proximal of the valve 143. The pressure sensor 138 may be located distal or proximal of the connector 144. The pressure sensor 138 may be communicatively coupled to the controller 150 to provide pressure measurement data to the controller 150.

In some embodiments, the system 100 can further include a second pressure sensor, or safety pressure sensor 139, coupled to the drainage tube 120. The safety pressure sensor 139 may be located distally of the valve 143 and configured to measure an internal pressure of the catheter lumen 114. The safety pressure sensor 139 may be communicatively coupled to the controller 150 to provide pressure measurement data to the controller 150.

The system 100 comprises the input airflow device 140 to provide a positive airflow 104 into the drainage tube 120 and thereby move fluid 123 proximally along the drainage tube 120 and into the collection container 130. The input airflow device 140 may be any device configured to provide airflow into the drainage tube 120. In some embodiments, the input airflow device 140 may be an electro-mechanical air pump. Such an air pump may be adjustable, i.e., capable of providing airflow at different rates. The input airflow device 140 may be continuously adjustable across a range of airflow rates or the input airflow device 140 may be discreetly adjustable across two, three, four, or more discreet, or predetermined, airflow rates.

In some embodiments, the input airflow device 140 may be a positive-displacement pump, e.g., a piston pump, such that a defined fluid volume is pumped with each cycle of the pump independent of back pressure. A positive-displacement pump may be advantageous in controlling the airflow rate with a controller. In other embodiments, the input airflow device 140 maybe a centrifugal pump, wherein the volumetric flow rate varies depending on back pressure. The non-positive-displacement operation of the centrifugal pump may be advantageous because the centrifugal pump may produce a low volumetric flow rate when the back pressure is elevated and automatically transition to an increased volumetric flow rate when the back pressure is decreased.

In some embodiments, the input airflow device 140 may comprise an air pressure source such as an air compressor tank combined with an adjustable valve. In such an embodiment, the valve may be modulated by the controller 150 to adjust the airflow rate and/or pressure delivered to the drainage tube 120. In some embodiments, the input airflow device 140 may comprise a peristaltic pump where a change in rotation of the peristaltic pump rollers modifies a rate of air flow delivered to the drainage tube 120.

In an embodiment, the system 100 may also comprise an output airflow device 145 coupled to the container 130 and/or to the drainage tube 120 at a proximal end 128 thereof. The output airflow device 145 may be coupled to the container 130 so that the airflow device 145 can draw air out of the container 130 while leaving the fluid 123 within the container 130 (e.g., act to suction air out of the container 130). More specifically, the output airflow device 145 may be coupled to the container 130 at an upper location of the container, i.e., above the liquid surface level within the container 130. The output airflow device 145 may comprise similar features and operating characteristics to the input airflow device 140. In some embodiments, the output airflow device 145 and the input airflow device 140 may comprise the same operating characteristics. In use, the output airflow device 145 may be configured to provide an airflow rate similar to an airflow rate of the input airflow device 140. In some embodiments, the airflow device 145 may be a vacuum.

In some embodiments of the system 100, the input airflow device 140 and the output airflow device 145 may be combined into a single airflow device. In such an embodiment, an output side of the single airflow device may be coupled to the drainage tube 120 and an input side of the single airflow device may be coupled to the container 130 to define a closed drainage tube clearing system. In such an embodiment, the output airflow from the system 100 is automatically matched to input airflow into the system 100 and can prevent inflation or deflation of the container 130.

In some embodiments, the system 100 may include a filter 146 disposed between the container 130 and the output airflow device 145. The filter 146 may be formed of a hydrophobic material. The filter 146 may allow airflow out of the container 130 and prevent liquid flow out of the container 130. By preventing liquid flow out of the container 130, the volume of drainage liquid may be accurately measured and the output airflow device 145 may be protected from liquid damage.

In an embodiment, the system 100 includes a controller 150 including a control logic 155. The controller 150 may include one or more of a microprocessor, memory, one or more logic engines, and an interface comprising one or more digital/analog inputs and outputs. The controller 150 maybe be configured to receive an input signal(s) and provide an output signal(s). The control logic 155 may be configured to monitor input signals and compare the input signals with one or more programmed limits as stored in memory. In some embodiments, the controller 150 may be a microcontroller, i.e., a small computer on a single integrated circuit comprising one or more CPUs (processor cores) along with memory and programmable input/output peripherals.

The controller 150 may be electrically coupled to one or more of the input airflow device 140, the output airflow device 145, the valve 143, the lumen pressure sensor 138 and the safety pressure sensor 139. The controller 150 may be configured to acquire pressure data from the pressure sensor 138 and/or the safety pressure sensor 139 which may include timed pressure data, i.e. where each pressure data point is associated with a time stamp. The controller 150 may process the pressure data in accordance with the control logic 155 to generate one or more parameters, such as a pressure parameter. The control logic 155 may apply mathematical, statistical, machine learning, artificial intelligence (AI), and/or other data processing operations to generate the parameters.

The control logic 155 may receive information, signals, and/or data from any or all of the pressure sensor 138, the valve 143, the input airflow device 140, the output airflow device 145 and the safety pressure sensor 139. The control logic 155 may also be configured to send information, signals, and/or data to one or more of the valve 143, the input airflow device 140, and the output airflow device 145. As such, the control logic 155 may control the operation of the valve 143, the input airflow device 140, and the output airflow device 145. The control logic 155 may be configured to apply data processing operations to the pressure data to generate parameters related to control of the valve 143, the input airflow device 140, and the output airflow device 145.

Figure 2B:
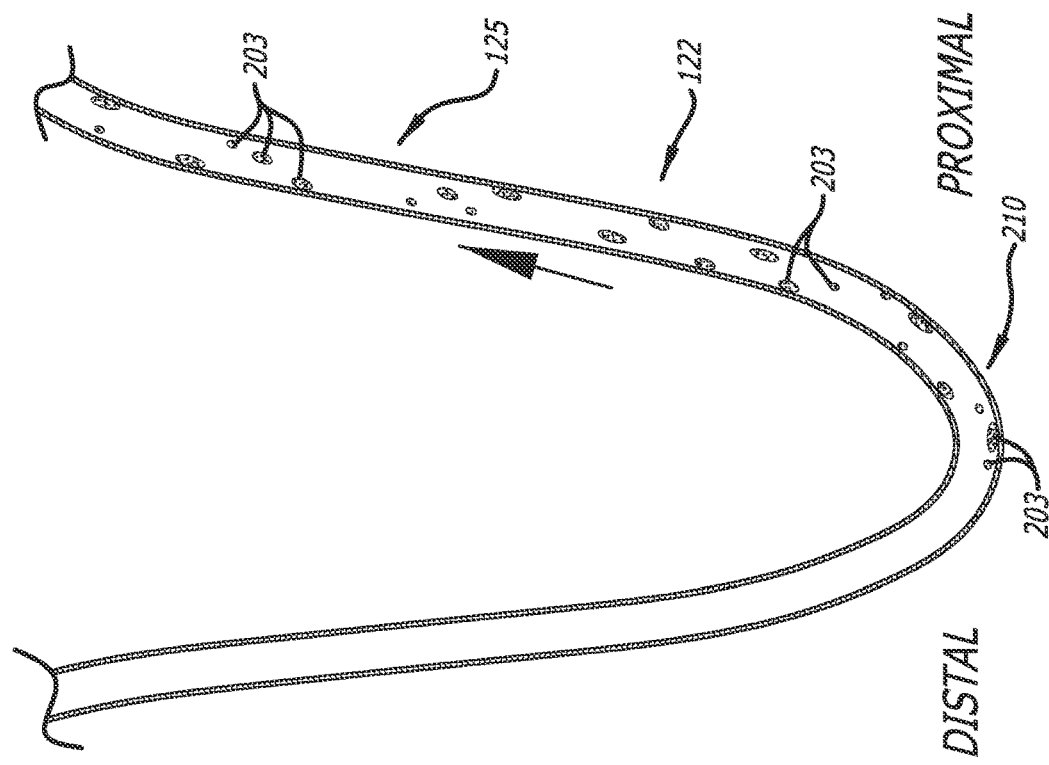
FIG. 2B illustrates fluid droplets within a dependent loop, in accordance with embodiments disclosed herein.
Figure 2A:
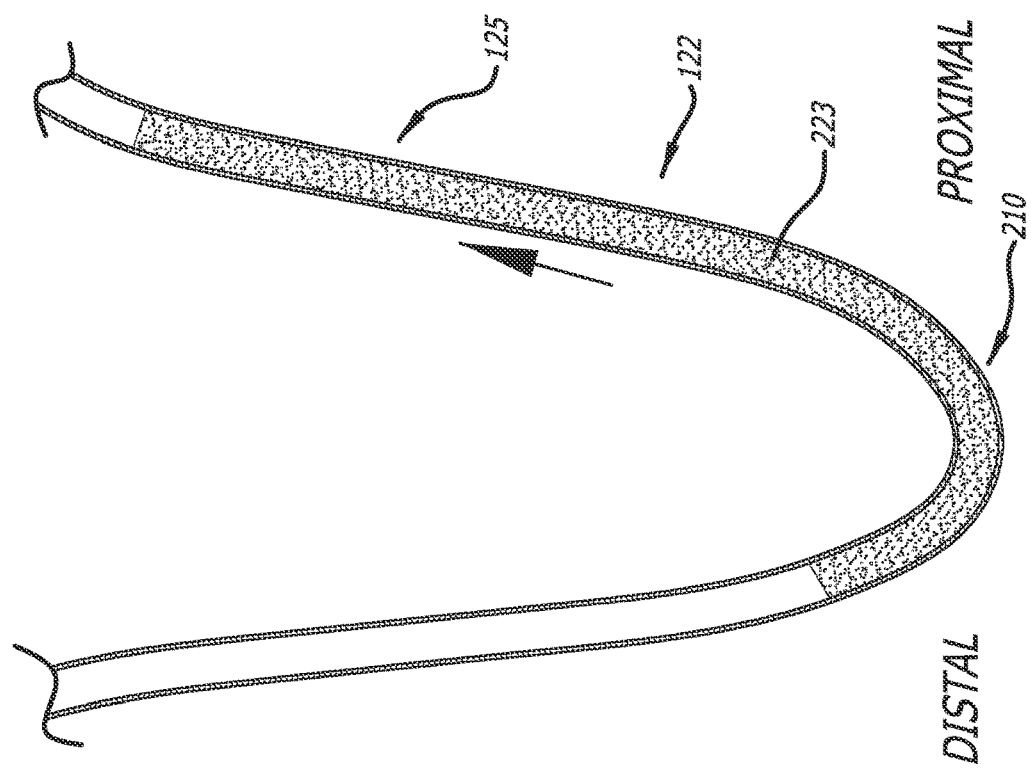
FIG. 2A illustrates a column of liquid within a dependent loop, in accordance with embodiments disclosed herein.

FIGS. 2A-2B illustrate a segment of the dependent loop 122 of the drainage tube 120 including a trough 210 and the incline 125. The fluid 123 disposed within the lumen 124 of the drainage tube 120 can form a liquid column 223 (FIG. 2A) or liquid droplets 203 (FIG. 2B). As shown in FIG. 2A, the liquid column 223 may extend from a distal side of the trough 210 to a proximal side of the trough 210. The liquid column 223 extends across the entire cross-sectional area of the drainage lumen 124. When the fluid 123 is in the form of the column 223, an internal air pressure of the drainage tube 120 distal of the column 223 may urge the column 223 proximally along the drainage tube 120. The pressure needed to move the column 223 up the incline 125 of the tubing 120 may be at least partially defined by a height of the liquid column 223.

FIG. 2B shows the fluid 123 in the form of droplets 203 disposed along the incline 125 of the drainage tube 120. The column 223 may generally break up into the droplets 203 when a distal end of the column 223 is disposed on the proximal side of the trough 210. When the fluid 123 is in the form of droplets 203, airflow may flow around the droplets 203. As such, the internal air pressure may not urge the fluid 123 in the form of droplets 203 proximally along the drainage tube 120. In this scenario, proximal displacement of the droplets 203 may rely on proximally oriented drag forces on the droplets 203 defined by an airflow rate rather than an internal pressure. The drag force is a function of the dynamic pressure of the airflow and the dynamic pressure is proportional to the airflow rate squared. As such, the airflow required to proximally urge to the droplets 203 along the drainage tube 120 may be greater than the airflow required to proximally urge to the column 223 along the drainage tube 120.

Figure 3:
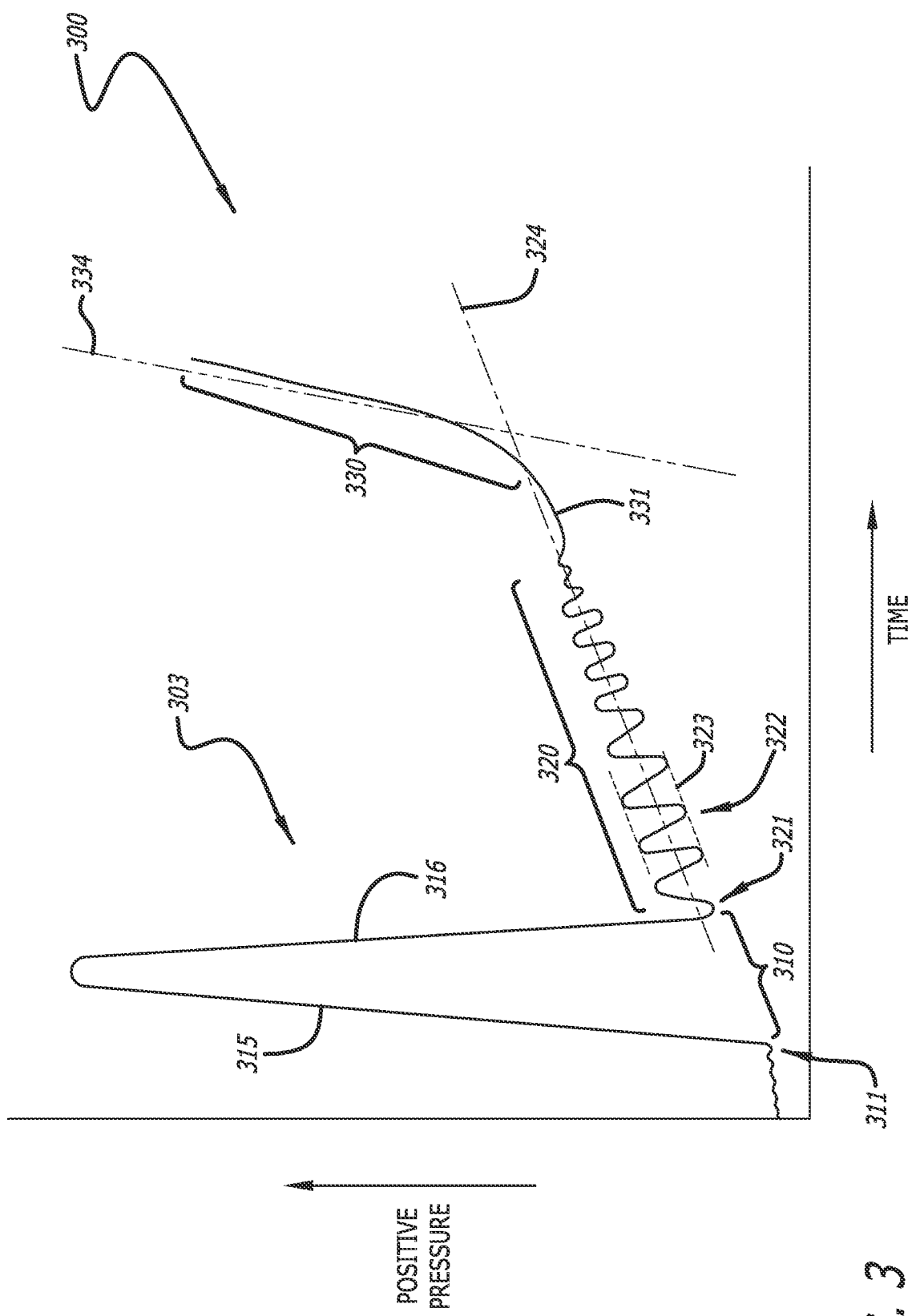
FIG. 3 shows a pressure chart for the fluid collection system of FIG. 1 illustrating a pressure profile when the output airflow devise does not remove air from the collection container, in accordance with embodiments disclosed herein.
Figure 4:
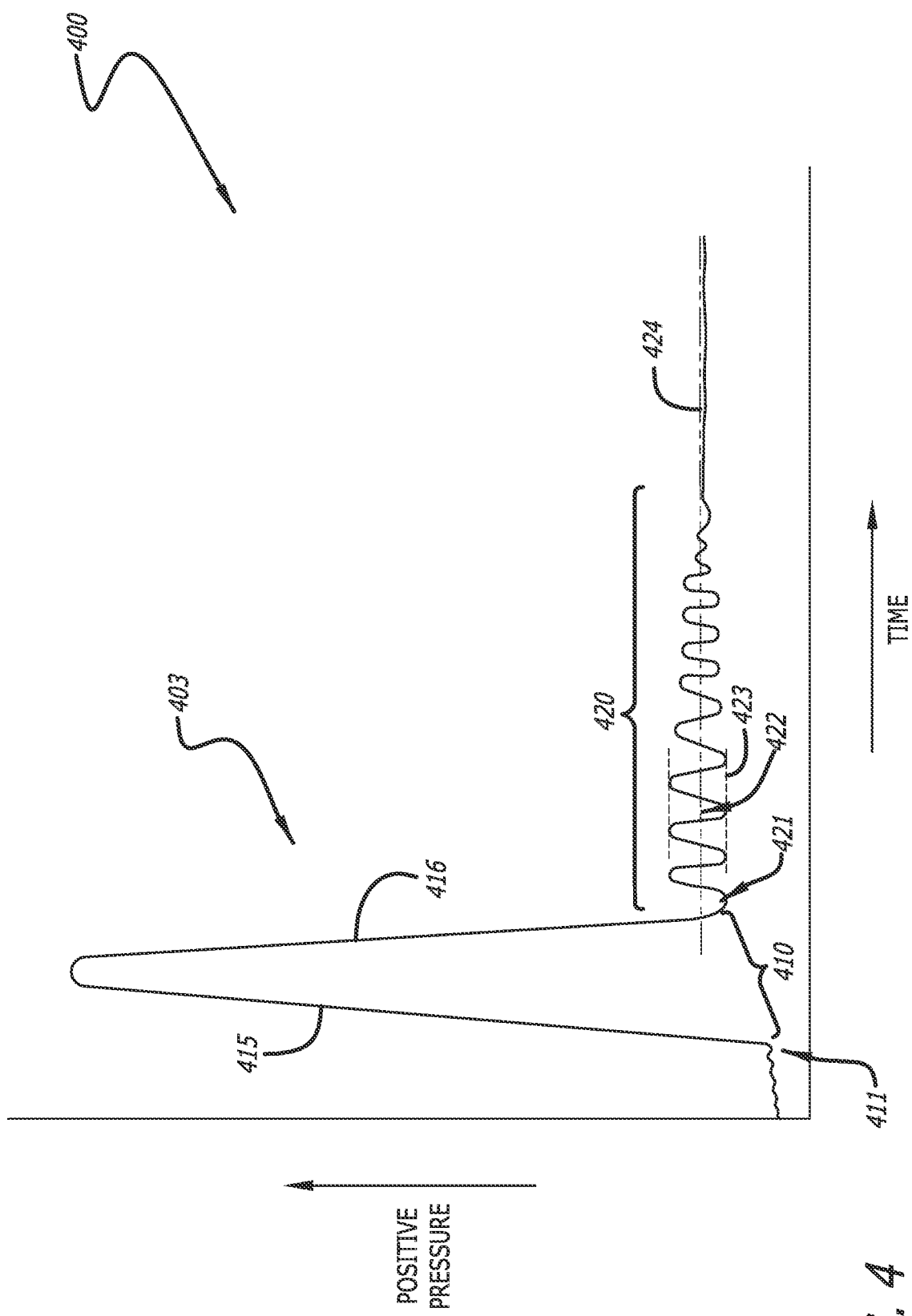
FIG. 4 shows a pressure chart for the fluid collection system of FIG. 1 illustrating a pressure profile when the output airflow devise does remove air from the collection container, in accordance with embodiments disclosed herein.

FIGS. 3-4 show pressure charts illustrating a pressure profile of exemplary pressures within the lumen 124 of the drainage tube 120 during operation of the system 100 when the collection container 130 is a bag. The operation represents the clearing process of fluid 123 from a dependent loop 122 as described above in relation to FIGS. 2A-2B. The pressure charts of FIGS. 3-4 include an x-axis representing time and a y-axis representing internal pressure of the drainage tube 120 as may be measured by the pressure sensor 138. Various events and stages of the pressure profile are defined for the purpose of description. FIG. 3 shows a chart 300 illustrating a pressure profile 303 in the event that the output airflow device 145 is absent or non-operational. FIG. 4 shows a chart 400 illustrating a pressure profile 403 in the event that the output airflow device 145 is present and operational.

FIG. 3 illustrates a pressure profile 303 including stages 310, 320, and 330 as described below. In addition to FIG. 3, the description below makes reference to FIGS. 1-2B. Prior to stage 310, the input airflow device 140 is inactive (off) and the valve 143 is open to allow fluid 123 to pass through the drainage tube 120. Stage 310 represents proximal displacement of the column 223 up the incline 125 and over the crest 126. Stage 310 begins with event 311 at which point the valve 143 is closed and the input airflow device 140 is activated to a first airflow rate. As airflow enters the drainage tube 120 between the valve 143 and the fluid column 223, the internal pressure of the drainage tube 120 is illustrated by the profile portion 315. The increasing internal pressure displaces the columnized liquid 223 proximally up the incline 125 of the drainage tube 120. As the liquid column 223 is displaced over the crest 126, the internal pressure of the drainage tube 120 decreases as illustrated by the profile portion 316. During the latter portion of stage 310, the liquid column 223 breaks up into droplets 203 further causing a decrease in internal pressure of the drainage tube 120 because airflow is allowed to pass proximally around and through the droplets 203. At the end of stage 310, the liquid column 223 has been displaced to the container 130 and leaving droplets 203 remaining in the drainage tube 120. As illustrated by the profile portion 316, a backpressure (blockage of airflow) may be less when the fluid 123 is in the form of droplets 203 than when the fluid 123 is in the form of a liquid column 223.

At the beginning event 321 of stage 320, the input airflow device 140 is transitioned to a second airflow rate that is greater than the first airflow rate. The second airflow rate produces a drag force on the droplets 203 to proximally urge the droplets 203 up the incline 125. During stage 320, the droplets 203 can break into smaller droplets 203 or combine into larger droplets 203, to cause a variation in internal pressure of the drainage tube 120. The pressure variation may be defined as a pressure noise 322 measured by the pressure sensor 138. As the drag force, displaces droplets 203 up the incline 125 and over crest 126, the level or magnitude 323 of the pressure noise 322 may decrease. As such, a decrease in the pressure noise level 323 may indicate a clearing progression of the droplets 203 from the drainage tube 120. At the end of stage 320, noise level 323 may have decreased sufficiently to represent an adequate clearing of the fluid 123 from the drainage tube 120. In some embodiments, the input airflow device 140 may be actively transitioned from a first airflow rate setting to a second airflow rate setting. In other embodiments, the input airflow device 140 may be configured to transition from the first airflow rate to the second airflow rate automatically and seamlessly as the backpressure decreases from stage 310 to the stage 320, such as a centrifugal air pump.

During stage 320, the airflow passing through the drainage tube 120 and into the container 130 causes the container 130 to expand at an early stage of expansion. Expansion of the container 130 during the early stage may define an increase of the internal pressure, i.e. a positive rate-of-change of internal pressure of the drainage tube 120 as indicated by the slope line 324. Early expansion of the container 130 (bag), may comprise a change in a shape of the bag. In some embodiments, a volume increase of the bag may be defined by a change from a flat shape toward a bulging shape without stretching the bag material. In some instances, early expansion of the bag may cause a relatively small positive rate-of-change of internal pressure of the drainage tube 120 as indicated by the slope line 324.

At the beginning event 331 of stage 330, the bag has begun a second stage of expansion, wherein a volume increase of the bag is defined by stretching of the bag material. The second stage of expansion causes the pressure to increase at a greater rate (more positive rate-of-change) than during the first stage of expansion as shown by the slope line 334 which has a greater slope than slope line 324. In some instances, a continued expansion of the bag as defined by stage 330 may result in fluid leakage from the bag or bursting of the bag.

FIG. 4 illustrates a pressure profile 403 including stages 410 and 420, as described below. In addition to FIG. 4, description below makes reference to FIGS. 1, 2A, and 2B. Similar to the pressure profile 303 of FIG. 3, prior to stage 410, the input airflow device 140 is inactive (off) and the valve 143 is open to allow fluid 123 to pass through the drainage tube 120. Similar to the profile 303 of FIG. 3, stage 410 begins with event 411 at which point the valve 143 is closed and the input airflow device 140 is activated to a first airflow rate. As airflow enters the drainage tube 120 between the valve 143 and column 223, internal pressure increases within the drainage tube 120 as illustrated by the profile portion 415. The increasing internal pressure displaces the column 223 proximally up the incline 125 of the drainage tube 120. As the column fluid 223 is displaced over the crest 126, the internal pressure within the drainage tube 120 decreases as illustrated by the profile portion 416. During the latter portion of stage 410, the column 223 breaks up into droplets 203 further causing a decrease in internal pressure within the drainage tube 120 because airflow is allowed to pass proximally around and through the droplets 203. At the end of stage 410, the column 223 has been displaced to the container 130 leaving only droplets 203 remaining in the drainage tube 120.

Similar to the pressure profile 303 of FIG. 3, at the beginning of stage 420, the input airflow device 140 is transitioned to a second airflow rate that is greater than the first airflow rate. The second airflow rate produces a drag force on the droplets 203 to proximally urge the droplets up the incline 125. As the droplets 203 move around in the drainage tube 120, the variation in backpressure created by the droplets 203 causes a pressure noise 422 measured by the pressure sensor 138. As the drag force, displaces droplets 203 up the incline 125 and over crest 126, the level or magnitude 423 of the noise 422 decreases. As such, the noise level 423 may be indicative of a volume of fluid 123 in the form of droplets 203 remaining in the drainage tube 120. At the end of stage 420, noise level 423 may have decreased sufficiently to represent an adequate clearing of fluid 123 from the drainage tube 120.

During stage 420, the output airflow device 145 may be activated to remove air from the container 130 and thereby inhibit expansion of the container 130. The output airflow device 145 may be activated to an airflow rate similar to the second airflow rate of the input airflow device 140 to compensate for the airflow into the drainage tube 120 by the input airflow device 140. As the airflow delivered into the drainage tube 120 by the input airflow device 140 is compensated for by the airflow removed from the container 130 by the output airflow device 145, expansion of the container 130 (bag) may be inhibited. As the container 130 does not expand, the internal pressure of the drainage tube 120, as measured by the pressure sensor 138, may remain constant as illustrated by the level slope line 424. In some embodiments, the output airflow device 145 may be activated at the beginning of stage 410, during stage 410, or at the beginning of stage 420.

The control logic 155 may generate pressure parameters related to the pressure profiles 303 and 403. The pressure parameters may include internal pressure of the drainage tube 120, pressure rate-of-change, and/or pressure noise. The pressure parameters may be running pressure parameters, i.e., dynamic pressure parameters that change in real time. The control logic 155 may apply mathematical, statistical, machine learning, artificial intelligence (AI), and/or other data processing operations to generate the pressure parameters. The pressure parameters may be generated from pressure data acquired from the pressure sensor 138 and, in some embodiments, the safety pressure sensor 139. The control logic 155 may compare the pressure parameters with pressure parameter limits and/or desired parameter values that are defined by the logic 255 and stored in memory. In response to the comparison, the control logic 155 send a signal to or otherwise modify the operation of the input airflow device 140, the output airflow device 145 and/or the valve 143.

The control logic 155 may be configured to initiate a tube clearing process in response to one or more acquired signals. In some instances, the control logic 155 may initiate a tube clearing process in response to a signal from a user action, such as pressing a button, for example. In some instances, the control logic 155 may initiate a tube clearing process according to a predefined time schedule. In some instances, the control logic 155 may initiate a tube clearing process if a defined parameter exceeds a predefined limit, or threshold.

As stated above, a pressure signal within the drainage tube 120 during the passive draining process may indicate pooling of fluid 123 in a dependent loop 122. In some embodiments, the control logic 155 may be configured to determine if fluid 123 is pooling in a dependent loop 122 and that clearing fluid 123 from the drainage tube 120 may be beneficial or needed. In some instances, pooling of fluid 123 may cause a change in internal pressure of the drainage tube 120 as may be measured by the pressure sensor 138. In some instances, the change may be an elevated internal pressure or a trend such as a positive rate-of-change of internal pressure. In other instances, the pooling of fluid 123 may cause a variability of the internal pressure of the drainage tube 120.

In some embodiments, the control logic 155 may acquire pressure data from the pressure sensor 138 in accordance with a pressure parameter to be employed during the passive operation of the drainage system. In some embodiments, the pressure parameter may be an internal pressure of the drainage tube 120. The control logic 155 may apply one or more data processing operations to generate the internal pressure of the drainage tube 120, such as filtering, for example. An elevated internal pressure may be indicative of pooling of fluid 123 within a dependent loop 122 of the drainage tube 120. The control logic 155 may compare the internal pressure with a high pressure limit for passive operation defined by the control logic 155. If the internal pressure exceeds the high pressure limit for passive operation, the control logic 155 may initiate the initiate a tube clearing process. Initiation of the tube clearing process may include closing the valve 143 and activating the input airflow source 140. In some embodiments, the control logic 155 may activate the input airflow source 140 to a first airflow rate.

In some embodiments, the pressure parameter to be employed during the passive operation of the drainage system may be a rate-of-change of the internal pressure. The control logic 155 may apply one or more data processing operations to generate the rate-of-change of the internal pressure internal pressure of the drainage tube 120, such as calculating a derivative of the internal pressure with respect to time, for example. A rate-of-change may be indicative of pooling of fluid 123 within a dependent loop 122 of the drainage tube 120. The control logic 155 may compare the rate-of-change with an upper rate-of-change limit for passive operation defined by the control logic 155. If the internal pressure exceeds the upper rate-of-change limit for passive operation, the control logic 155 may initiate the tube clearing process.

In some embodiments, the control logic 155 may acquire pressure data from the pressure sensor 138 in accordance with a pressure parameter to be employed during the tube clearing process. In some embodiments, the pressure parameter may be running rate-of-change of the internal pressure of the drainage tube 120. The control logic 155 may apply one or more data processing operations to generate the running rate-of-change for the tube clearing process. The running rate-of-change may be indicative over inflation or collapsing of the collection container 130. The control logic 155 may compare the running rate-of-change of the internal pressure with a desired rate-of-change for the tube clearing process defined by the control logic 155 which may be about "0" zero. In response to the comparison, the control logic 155 may adjust the airflow rate of the output airflow device 145 to move the running rate-of-change toward the desired rate-of-change. If the running rate-of-change is positive indicating inflation of the collection container 130, the control logic 155 may increase the airflow rate of the output airflow device 145. If the running rate-of-change is negative indicating collapsing of the collection container 130, the control logic 155 may decrease the airflow rate of the output airflow device 145.

In some embodiments, in response to the comparison, the control logic 155 may adjust the airflow rate of the input airflow device 140 to move the running rate-of-change toward the desired rate-of-change of the internal pressure of the internal pressure. If the running rate-of-change is positive indicating inflation of the collection container 130, the control logic 155 may decrease the airflow rate of the input airflow device 140. If the running rate-of-change is negative indicating collapsing of the collection container 130, the control logic 155 may increase the airflow rate of the input airflow device 145.

In some embodiments, the control logic 155 may acquire pressure data from the pressure sensor 138 in accordance with another pressure parameter to be employed during the tube clearing process. In some embodiments, the pressure parameter may be running pressure noise level. The control logic 155 may apply one or more data processing operations to generate the running pressure noise level, such as calculating a standard deviation, for example. The running pressure noise level may be indicative of the presence of droplets 203 within a dependent loop 122 of the drainage tube 120. The control logic 155 may compare the running pressure noise level with an upper noise level limit defined by the control logic 155. If the running pressure noise level exceeds the upper noise level limit, the control logic 155 may transition the input airflow device 140 from a first airflow rate to a second air flow to clear the droplets 203 from the drainage tube 120.

In some embodiments, the control logic 155 may compare the real-time pressure noise level with a lower noise level limit. A reduced real-time pressure noise level may be indicative of the elimination of droplets 203 from the dependent loop 122 and that continuing the tube clearing process may not be advantageous. The control logic 155 may then deactivate the input airflow device 140, the output airflow device 145, and open the valve 143.

In some embodiments, the control logic 155 may be configured to monitor one or more pressure parameters during the tube clearing process and take corrective action such as discontinuing the tube clearing process to prevent an undesirable or unsafe event from occurring. In some embodiments, a pressure parameter may be the internal pressure of the drainage tube 120. The control logic 155 may compare the internal pressure parameter with a positive pressure limit for the tube clearing process defined by the control logic 155. The control logic 155 may then deactivate the input airflow device 140 if the internal pressure exceeds the positive pressure limit for the tube clearing process. An elevated internal pressure parameter may be indicative of an occlusion or blockage of the drainage tube 120 and deactivating the input airflow device 140 may cause the internal pressure to be reduced.

In some embodiments, the control logic 155 may compare the internal pressure with a negative pressure limit defined by the control logic 155. The control logic 155 may then deactivate the output airflow device 145 if the internal pressure exceeds the negative pressure limit. An excessively negative internal pressure of the drainage tube 120 may be indicative of collapsing of the collection container 130 and deactivating the input airflow device 140 may cause the internal pressure to increase.

In some embodiments, a pressure parameter may be a running rate-of-change of internal pressure. The control logic 155 may compare the running rate-of-change of internal pressure with a positive rate-of-change limit for the tube clearing process defined by the control logic 155. The control logic 155 may then deactivate the input airflow device 140 if the running rate-of-change exceeds the positive rate-of-change limit. An elevated running rate-of-change of internal pressure may be indicative of over-inflation of the collection container 130 and deactivating the input airflow device 140 may inhibit inflation of the collection container 130.

In some embodiments, the control logic 155 may compare the running rate-of-change of internal pressure with a negative rate-of-change limit for the tube clearing process defined by the control logic 155. The control logic 155 may then deactivate the output airflow device 140 if the running rate-of-change of internal pressure exceeds the negative rate-of-change limit. An excessively negative real-time rate-of-change of internal pressure may be indicative of collapsing of the collection container 130 and deactivating the output airflow device 140 may inhibit collapsing of the collection container 130.

In some embodiments, the control logic 155 may be configured to monitor pressure data acquired from the safety pressure sensor 138. In some embodiments, the control logic 155 may process acquired pressure data from the pressure sensor 138 in accordance with an internal pressure parameter of the catheter 110. The control logic 155 may compare the internal pressure of the catheter with a positive safe pressure limit defined by the control logic 155. The control logic 155 may then deactivate the input airflow device 140 if the internal pressure of the catheter 110 exceeds the positive safe pressure limit. An elevated catheter pressure may be indicative of a failure of the valve 143 and deactivating the input airflow device 140 may cause the internal pressure of the catheter to be reduced.

The control logic 155 may compare the internal pressure of the catheter with a negative safe pressure limit defined by the control logic 155. The control logic 155 may then deactivate the output airflow device 145 if the internal pressure of the catheter 110 exceeds the negative safe pressure limit. An excessively negative catheter pressure may be indicative of a failure of the valve 143 and deactivating the output airflow device 145 may cause the internal pressure of the catheter to be less negative.

Catheter Occlusion Systems

As discussed herein an input airflow device 140 can provide a positive air pressure 104 which can be introduced to the drainage lumen 124 at a connector 144, disposed proximate the catheter 110 (FIG. 1). In an embodiment, the connector 144 can be a sample port, or similar structure. As shown in FIG. 1, the positive air pressure 104 can urge fluid through the drainage tube 120 and into the collection container 130. In an embodiment, the positive air pressure 104 can clear fluid caught in dependent loops 122, into the collection container 130. As will be appreciated, the positive air pressure 104 can create a pressure differential within the fluid drainage system which can be detrimental to the patient. In an embodiment, the system 100 can include a valve system ("valve") 143 configured to control a distal fluid flow and protect the patient from any detrimental effects of a pressure spike within the drainage lumen 124 of the system 100.

FIGS. 5-9E show various embodiments of valve systems, or catheter occlusion systems, which can be used in addition to or in place of the valve 143. The catheter occlusion systems can be coupled with the controller 150 and can be configured to transition between an open position and a closed position, as described herein. In an embodiment, the controller 150 can be coupled with an airflow device, pump, or the like (e.g. input airflow device 140) which in turn can provide a positive or negative air flow to the catheter occlusion system (e.g. by way of inflation line 548) and can transition the catheter occlusion system between an open and a closed position.

Figure 6B:
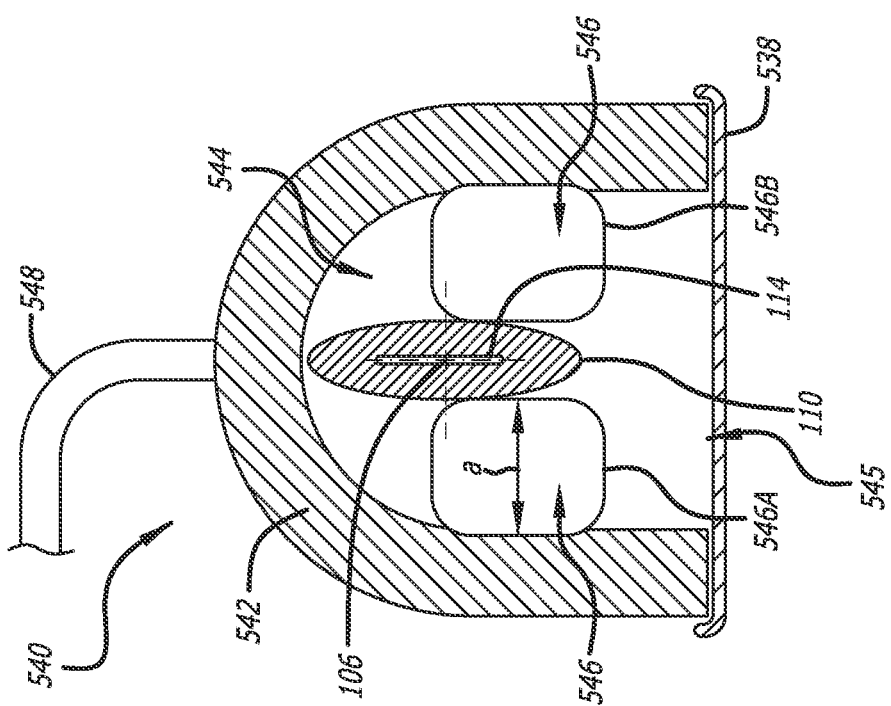
FIG. 6B shows a cross sectional view of a catheter occlusion system coupled with a catheter in an inflated state, in accordance with embodiments disclosed herein.
Figure 6A:
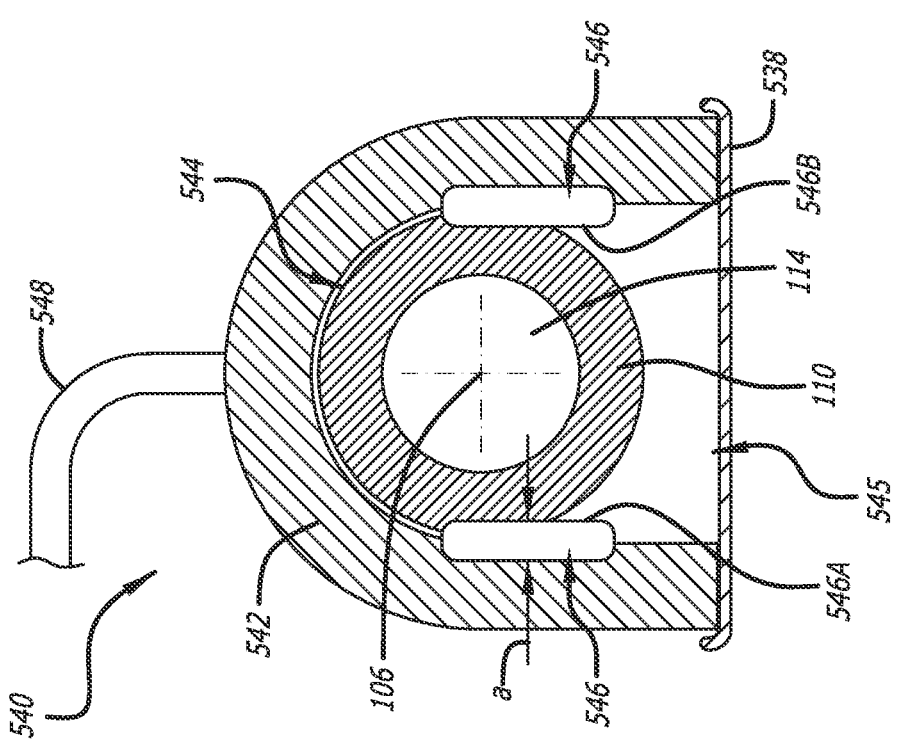
FIG. 6A shows a cross sectional view of a catheter occlusion system coupled with a catheter in a deflated state, in accordance with embodiments disclosed herein.
Figure 6D:
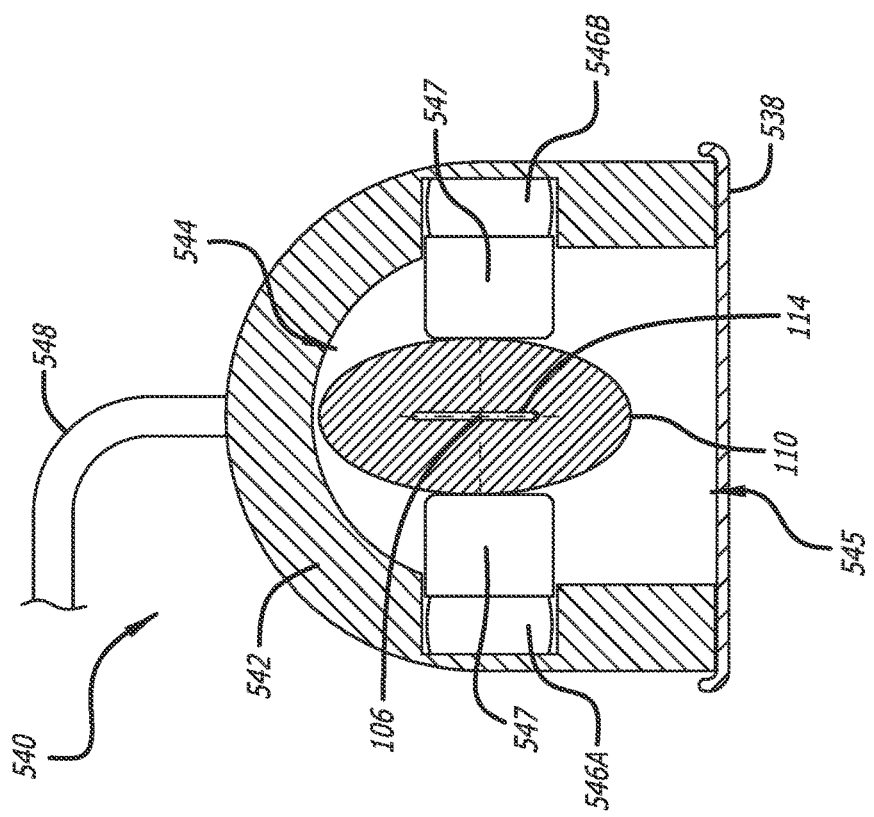
FIG. 6D shows a cross sectional view of a catheter occlusion system coupled with a catheter in an extended state, in accordance with embodiments disclosed herein.

As shown in FIGS. 5-6D, in an embodiment, the valve 143 can include a catheter occlusion system 540 which can be coupled to the catheter 110 and configured to transition to between an open position (FIGS. 6A, 6C) and a closed position (FIGS. 6B, 6D). In the closed position, the catheter occlusion system 540 can occlude the catheter lumen 114 and prevent fluid from entering the catheter lumen 114 when the positive air pressure 104 is introduced to the system 100. The catheter occlusion system 540 can occlude the catheter lumen 114 distally of the connector 144 to prevent fluid, e.g. liquid or gas, from flowing distally through the catheter lumen 114. For example, the catheter occlusion system 540 can occlude the catheter lumen 114 prior to, or at the same time as, the introduction of a positive air pressure 104 at the connector 144. The catheter occlusion system 540 can protect the patient from pressure differentials within the system 100, or prevent fluid from flowing distally through the catheter 110 and into the patient, which can be detrimental to the patient.

The catheter occlusion system 540 can be coupled to an exterior portion of the catheter 110 to occlude the catheter lumen 114. Advantageously, the catheter occlusion system 540 can be coupled to, or removed from, a catheter 110 that is already placed within the patient and can maintain the integrity of the closed, sterile fluid collection system 100, mitigating the introduction of pathogens. Further, the catheter 110 can be formed of an elastic material, for example natural rubber latex ("NRL"), synthetic rubber, latex, silicone, elastomer, or the like, that displays elastic mechanical properties and can resist permanent deformation even when subjected to prolonged or repeated deformation. This can contrast with materials that form the drainage tube 120 that can display more visco-elastic properties, required to maintain a shape and mitigate the formation of dependent loops, e.g. dependent loop 122. As a result, the drainage tube 120 can be more susceptible to permanent deformation relative to the catheter 110.

FIGS. 6A-6D show further details of a catheter occlusion system 540. In an embodiment, the catheter occlusion system 540 can generally include a body 542 defining a channel 544, an inflation chamber 546, and an inflation line 548 fluidly coupled to the inflation chamber 546. In an embodiment, the catheter occlusion system 540 can be a cuff system configured to be "clipped on" to the catheter 110.

The body 542 of the catheter occlusion system 540 can be formed of a substantially rigid material and define a channel 544 configured to receive a portion of the catheter 110 therein. Exemplary rigid materials can include, but not limited to, plastic, polymer, metal, alloy, composite, acrylonitrile butadiene styrene ("ABS"), polycarbonate plastic ("PC"), polyethylene plastic ("PE"), thermoplastic polyurethane ("TPU"), combinations thereof, or the like. As shown in FIGS. 6A-6D, a cross-sectional shape of the body 542 can define a substantially "horse-shoe" shape to define an elongate opening 545 to the channel 544 to allow ingress or egress of the catheter 110 therefrom. However, it will be appreciated that other cross-sectional shapes such as a "C-shape," "U-shape," or the like, are also contemplated.

The channel 544 can extend substantially parallel to the longitudinal axis of the catheter 110. The body 542 can encircle a portion of the catheter 110 about the longitudinal axis of the catheter 110. In an embodiment, the body 542 encircles the catheter 110 through an arc of between 180° and 350°, although greater or lesser arcs are also contemplated. In an embodiment, the body 542 can encircle the catheter completely, i.e. through an arc of 360°. The body 542 can define a longitudinal length, extending parallel with a longitudinal axis of the catheter. In an embodiment, the longitudinal length of the body 542 can be between 0.5 cm and 3 cm, although greater or lesser longitudinal lengths are also contemplated.

In an embodiment, as shown in FIG. 5, the body 542 can be sized to engage a portion of the catheter 110 disposed between a bifurcation 116 and proximal end 118 of the catheter 110. As such, the catheter occlusion system 540 can engage and occlude a portion of the catheter 110 that defines only the catheter lumen 114. This can avoid occluding portions of the catheter 110 that are distal of the bifurcation 116 and can include inflation lumens, sampling lumens, flushing lumens, or the like where occlusions could be detrimental to the functioning of the catheter 110.

In an embodiment, the catheter occlusion system 540 can include an inflation chamber 546, such as an inflatable balloon, a piston chamber including a piston head, or the like, that can transition between an inflated or extended state, and a deflated or retracted state, to transition the catheter occlusion system 540 between a closed and open state respectively.

As shown in FIGS. 6A-6B, in an embodiment, the inflation chamber 546 can include an inflatable balloon, disposed in a wall of the channel 544 and can transition between an inflated state, such that the catheter occlusion system 540 is in a closed position, and a deflated state such that the catheter occlusion system 540 is in an open position. In a deflated state, the balloon 546 can retract and allow for ingress or egress of the catheter 110 to/from the channel 544. In an embodiment, the balloon 546 can contact the catheter 110 in the deflated state to maintain engagement between the catheter occlusion system 540 and the catheter 110.

Figure 6C:
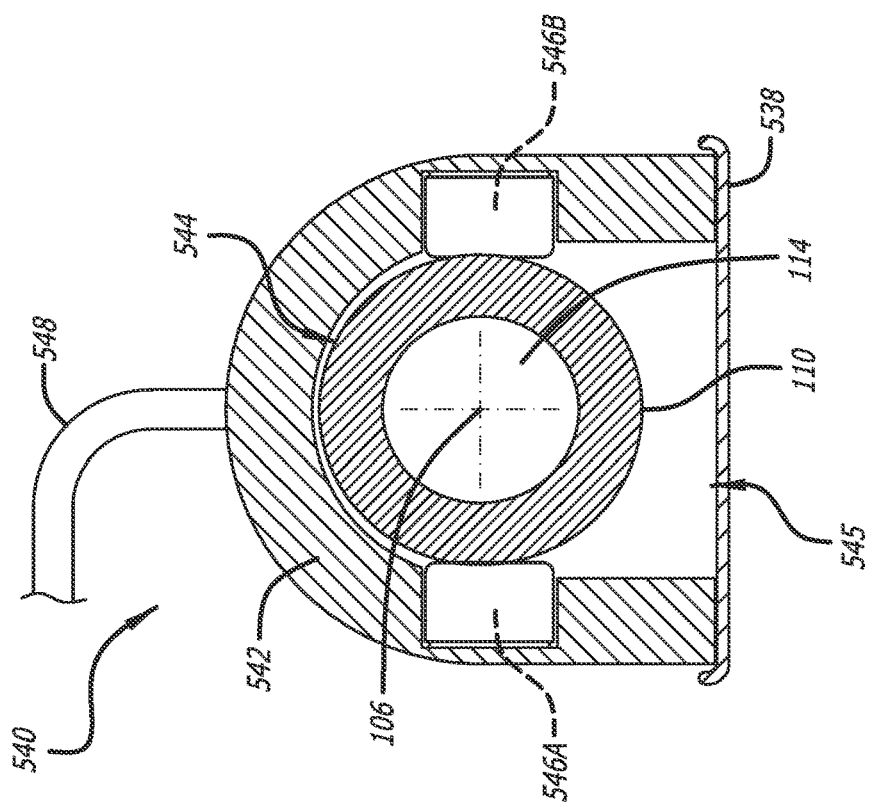
FIG. 6C shows a cross sectional view of a catheter occlusion system coupled with a catheter in a retracted state, in accordance with embodiments disclosed herein.

In an embodiment, as shown in FIGS. 6C-6D, the inflation chamber 546 can be a piston chamber having a piston head 547 slidably engaged therewith, and configured to transition between a retracted state such that the catheter occlusion system 540 is in an open position (FIG. 6C) and an extended state such that the catheter occlusion system 540 is in a closed position (FIG. 6D). Advantageously, the surface of the balloon 546 or the surface of the piston head 547 can provide a dispersed area of pressure and prevent kinking or cutting of the catheter 110, mitigating damage to the catheter 110 after prolonged or repeated inflation.

In an embodiment, one or more of a surface of the channel 544, a surface of the balloon 546, or a surface of the piston head 547 can include an adhesive, configured to adhere to a surface of the catheter 110 to retain the catheter occlusion system 540 thereto. In the closed position, the inflation chamber 546 or piston head 547 can compress the portion of the catheter 110 disposed within the channel 544 to occlude the catheter lumen 114 and prevent any fluid flow through the catheter lumen 114. In an embodiment, the inflation chamber 546 can be partially inflated to partially occlude the catheter lumen 114 to between 0% and 100% occlusion of the catheter lumen 114. In an embodiment, a user can modify the amount of inflation of the inflation chamber 546 and thereby modify the percentage amount of occlusion of the catheter lumen 114. Deflating the inflation chamber 546 can allow the elasticity of the catheter to resume the unstressed state, and allow the catheter lumen 114 to resume an un-occluded state (i.e. an open position).

In an embodiment, a vacuum can be applied to the inflation chamber 546 to actively transition the balloon or piston head 547 from the inflated position to the deflated position, transitioning the catheter occlusion system 540 from the closed position to the open position. Advantageously, where a surface of the balloon 546 or piston head 547 is adhered to the catheter 110, active deflation can facilitate restoring patency to the catheter lumen 114. In an embodiment, a pressure can be released from the inflation chamber 546 to allow the balloon or piston head 547 to passively transition from the inflated position to the deflated position. In an embodiment, the elasticity of the balloon can allow the balloon to transition between the inflated position and the deflated position. In an embodiment, the piston chamber can include a biasing member, e.g. spring or the like, coupled between a wall of the piston chamber 546 and a surface of the piston head 547 and configured to bias the piston head 547 towards the retracted state.

In an embodiment, as shown in FIGS. 6A-6B, the inflation chamber 546 can be positioned in a side wall of the channel 544 and can be configured to expand and retract along an inflation axis (a) extending perpendicular to the longitudinal axis of the catheter 110. In an embodiment, the inflation chamber 546 can be positioned such that the inflation chamber 546 can expand and retract along an inflation axis (a) that is disposed between the channel opening 545 and a radial midpoint of the catheter 110. The radial mid-point of the catheter being substantially aligned with a central longitudinal axis 106 of the catheter. As such, as the inflation chamber 546 expands, the inflation chamber 546 can compress the catheter 110 into the channel 544 and retain the catheter 110 within the channel 544.

In an embodiment, the inflation chamber 546 can be inflated using an inflation fluid. The inflation fluid can be either a liquid (hydraulic) or a gas (pneumatic). Exemplary inflation fluids can include compressed gas, air, water, hydraulic oil, or the like. The catheter occlusion system 540 can further include an inflation line 548 that is in fluid communication with the inflation chamber 546 and configured to provide the inflation fluid thereto.

In an embodiment, the catheter occlusion system 540 can include a first inflation chamber 546A disposed in a first side wall of the channel 544 and a second inflation chamber 546B disposed in a second side wall of the channel 544, opposite the first inflation chamber 546A across the central longitudinal axis 106. The first inflation chamber 546A and the second inflation chamber 546B can be inflated and deflated concurrently, to expand and contract along an inflation axis (a) extending perpendicular to the central longitudinal axis 106. As such, the inflation chambers 546A, 546B, can compress the catheter 110 therebetween, occluding the catheter lumen 114. In an embodiment, the inflation/deflation axis (a) of the inflation chambers 546A, 546B can be aligned with the central longitudinal axis 106. In an embodiment, the inflation/deflation axis (a) of the inflation chambers 546A, 546B can be offset from the central longitudinal axis 106 and aligned between the central longitudinal axis and the channel opening 545, as shown in FIGS. 6A-6B. Advantageously, the offset axis (a) can both compress the catheter 110 between the inflation chambers 546A, 546B, as well as urge the catheter 110 into the channel 114 mitigating accidental disengagement of the catheter occlusion system 540 from the catheter 110. In an embodiment, the first inflation chamber 546 and the second inflation chamber 546B can be inflated or deflated independently of each other to selectively occlude the catheter lumen 114.

In an embodiment, the catheter occlusion system 540 can further include a strap 538 extending perpendicular to the longitudinal axis 106 and extending across the channel opening 545. The strap 538 can be configured to prevent accidental disengagement of the catheter occlusion system 540 from the catheter 110. The strap 538 can be selectively released to allow for ingress/egress of the catheter 110 from the channel 544. The strap can include a buckle, hook and loop attachment, adhesive, or the like to selectively secure the strap 538 in place.

In an embodiment, as shown in FIGS. 7A-7D, a catheter occlusion system 640 can include a body 642, formed of a rigid material that fully encircles the catheter 110 about the longitudinal axis 106. The body 642 can be formed of a first body portion 642A and a second body portion 642B that can be releasably coupled together to form the body 642 and define a channel 644 through which a portion of the catheter 110 extends. In an embodiment, the first body portion 642A and the second body portion 642B can engage in an interference fit, press-fit, or snap-fit engagement. In an embodiment the body 642 can include a latch, clasp, hinge, living hinge, combinations thereof, or the like, to couple the first body portion 642A with the second body portion 642B. Selectively releasing the second body portion 642B from the first body portion 642A can allow for ingress or egress of the catheter 110 to/from the channel 544.

In an embodiment, the catheter occlusion system 640 can include four inflation chambers 646 disposed radially evenly about the central longitudinal axis 106. Each of the inflation chambers 646 can be fluidly coupled with the inflation line 548 by way of one or more inflation channels 648 extending through the body 642. It will be appreciated, however, that the catheter occlusion system 640 can include various numbers, positions, and configurations of inflation chambers 646 without limitation. Further, the inflation chambers 646 can be dispersed radially evenly or radially unevenly about the longitudinal axis 106. In an embodiment, the inflation channel 648 can extend through the body 642 to fluidly couple inflation chamber(s) 646 with the inflation line 548. As shown in FIG. 7D, each of the inflation chambers 646 can inflate along an axis (a) that extends perpendicular to the longitudinal axis 106. The inflation chambers 646 can inflate and expand concurrently to compress the catheter 110 therebetween and occlude the catheter lumen 114.

Figure 7A:
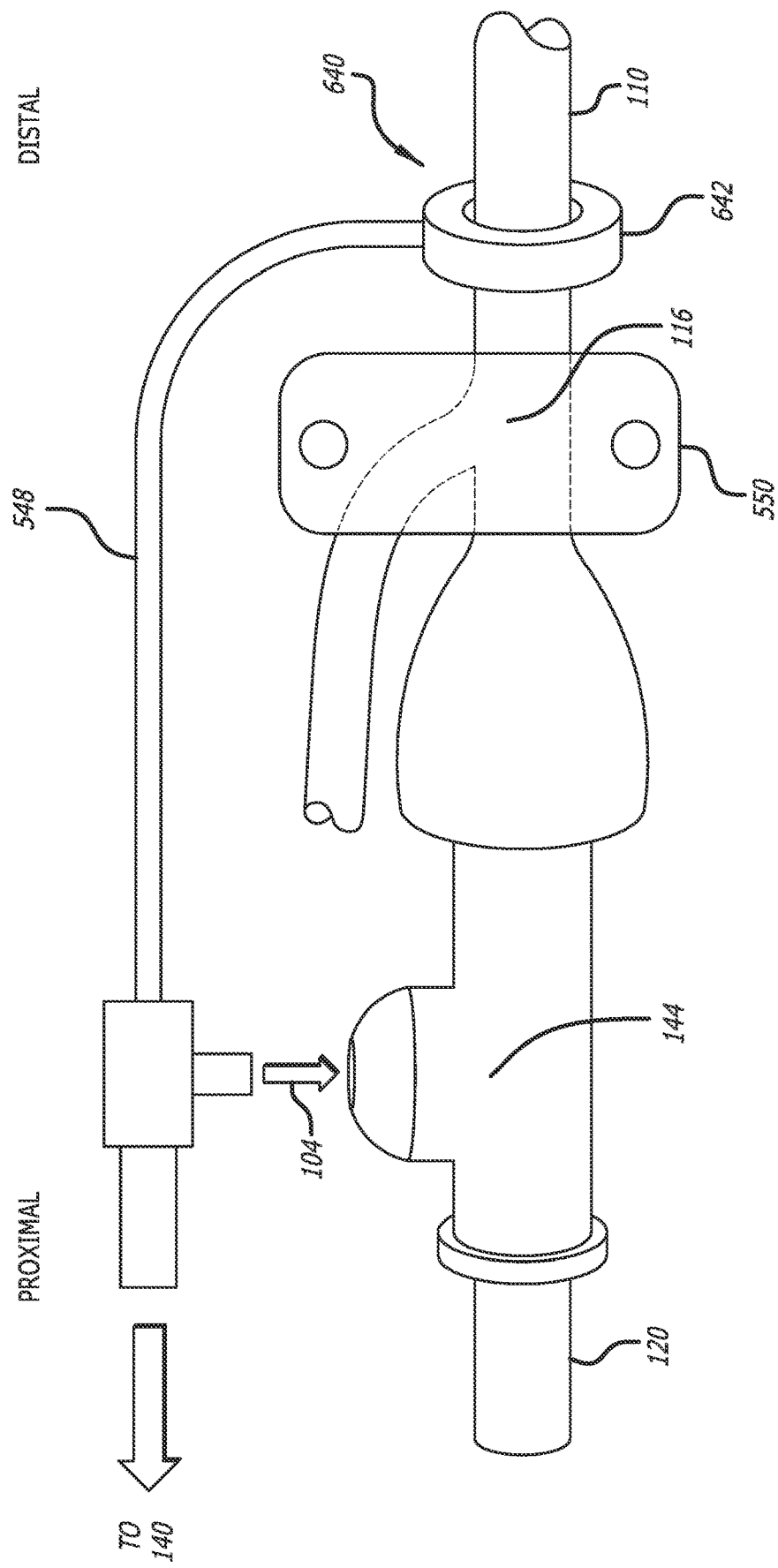
FIG. 7A shows a perspective view of a catheter occlusion system coupled with a catheter, in accordance with embodiments disclosed herein.
Figure 7B:
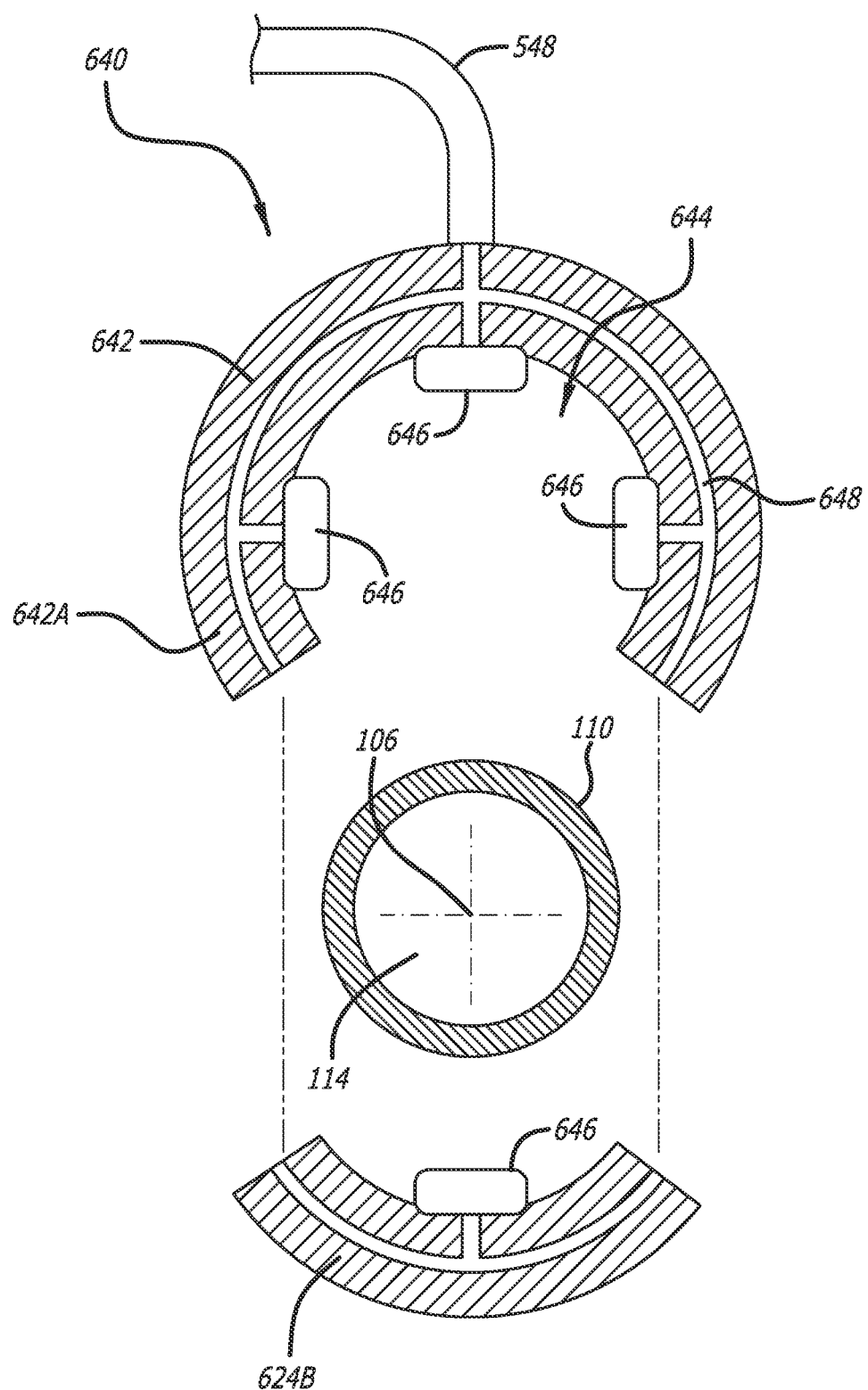
FIG. 7B shows a cross-section view of a catheter occlusion system and a catheter, in accordance with embodiments disclosed herein.
Figure 7D:
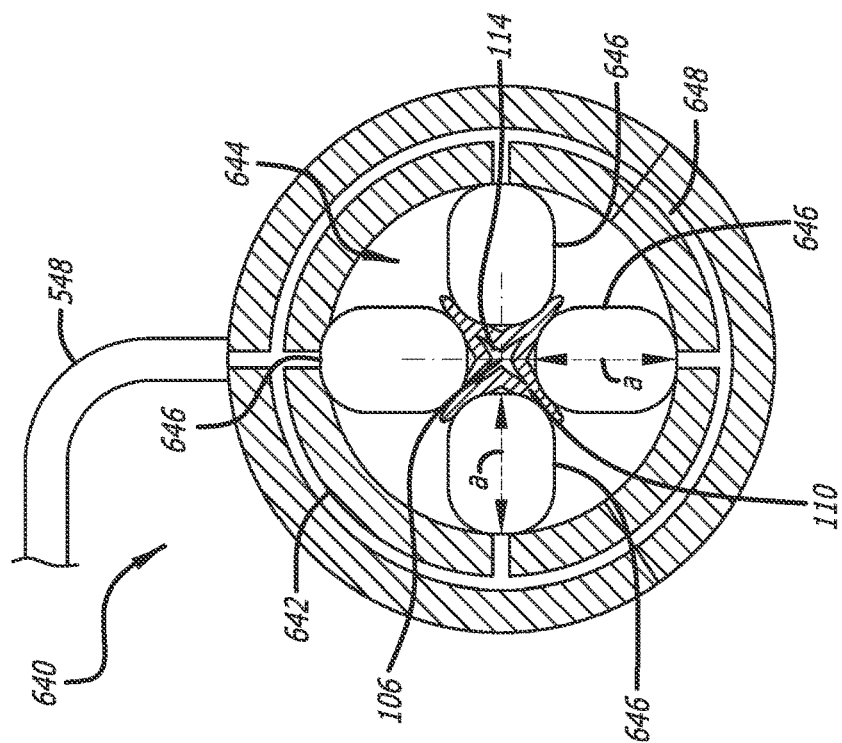
FIG. 7D shows a cross sectional view of a catheter occlusion system coupled with a catheter in an inflated state, in accordance with embodiments disclosed herein.
Figure 7C:
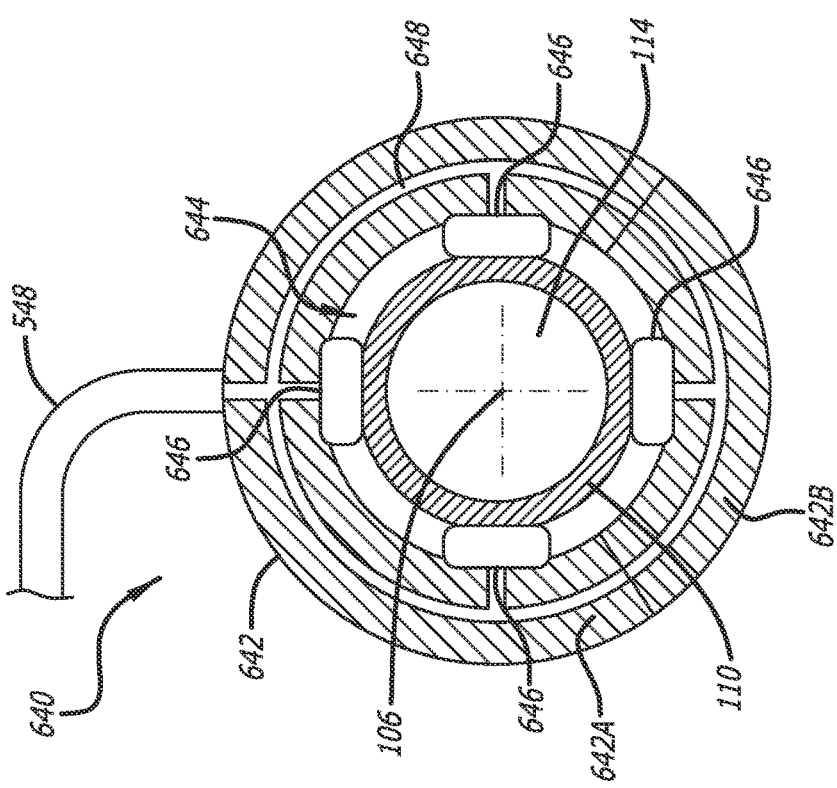
FIG. 7C shows a cross sectional view of a catheter occlusion system coupled with a catheter in a deflated state, in accordance with embodiments disclosed herein.

In an embodiment, as shown in FIG. 7A, the inflation line 548 can be fluidly coupled to the input airflow device 140 that is also in fluid communication with the connector 144. As such, a positive air pressure 104 can simultaneously inflate inflation chamber(s) 646 and introduce a positive air pressure to the drainage lumen 124 by way of connector 144. The inflation chambers 646 can occlude the catheter lumen 114 to prevent the positive air pressure 104 introduced at the connector 144 from flowing distally through the catheter lumen 114. In an embodiment, the catheter occlusion system 640 can be coupled to the catheter 110 either distally or proximally of the bifurcation 116. In an embodiment, the catheter 110 can be secured to the patient using a stabilizing device 550, or the like. Optionally, the stabilization device 550 can be coupled to the catheter bifurcation 116 and secure the catheter 110 to the patient.

Advantageously, coupling the inflation line 548 with the input airflow device 140 of the system 100 can allow for automation of the occlusion of the catheter lumen 114. The catheter lumen 114 can be occluded, partially occluded, or unconcluded, and can be synchronized with the activation and deactivation of the active clearing system 100. This can alleviate the work load for hospital staff and can provide more reliable clearing of dependent loops 122, which in turn can mitigate CAUTI or similar HAI. Further the automation of the catheter occlusion system can allow for rapid cycling of occlusions, or for accurate calibration of partial occlusions, where advantageous.

Figure 8A:
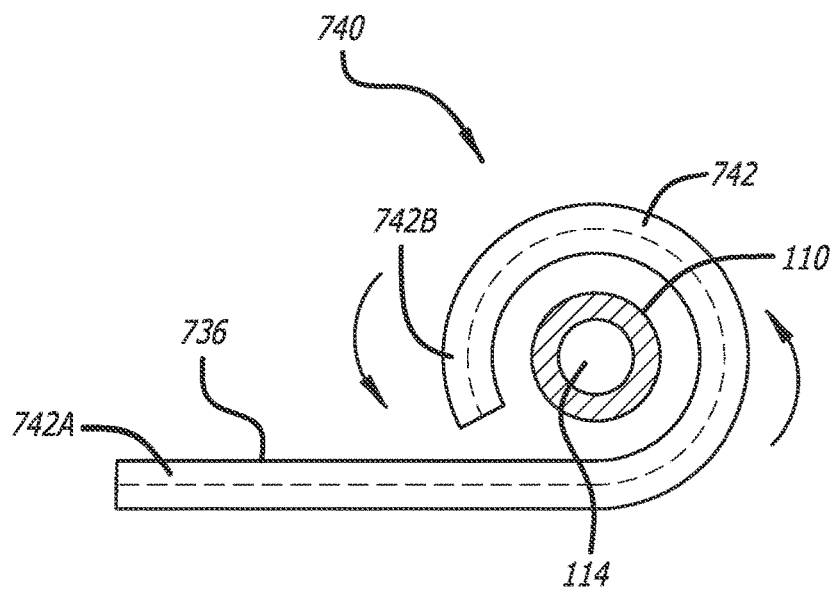
FIG. 8A shows a cross-section view of a catheter occlusion system and a catheter, in accordance with embodiments disclosed herein.
Figure 8B:
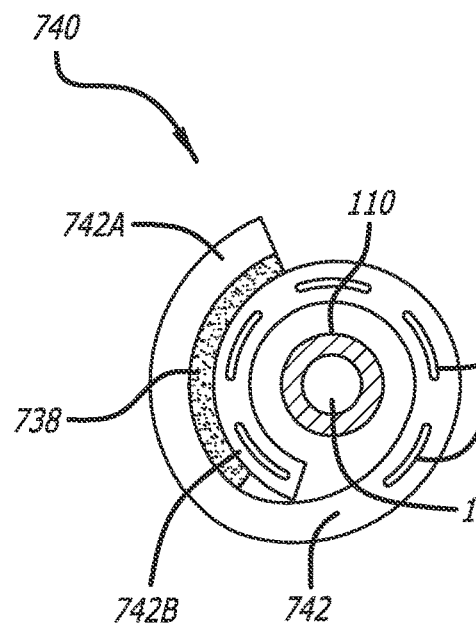
FIG. 8B shows a cross sectional view of a catheter occlusion system coupled with a catheter in a deflated state, in accordance with embodiments disclosed herein.
Figure 8C:
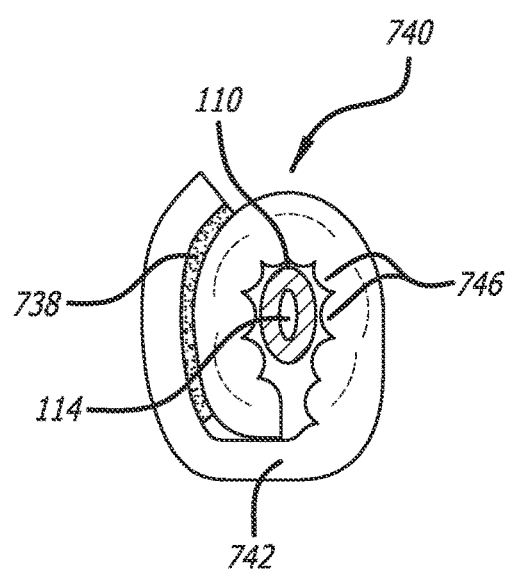
FIG. 8C shows a cross sectional view of a catheter occlusion system coupled with a catheter in an inflated state, in accordance with embodiments disclosed herein.

In an embodiment, as shown in FIGS. 8A-8C, a catheter occlusion system 740 can include a flexible body 742 that is configured to wrap around the catheter 110 about the longitudinal axis. The flexible body 742 can extend through an arc of more that 360° about the longitudinal axis of the catheter 110. A first end of the flexible body 742A can releasably engage a second end 742B of the body 742, disposed opposite the first end 742A. The flexible body 742 can include a releasable engagement 738 to couple the first end 742A to the second end 742B. Exemplary releasable engagements 738 can include a buckle, clasp, latch, hook and loop attachment, adhesive, combinations thereof, or the like.

One or more inflation chambers 746 can be disposed on a first surface 736 of the body 742 or disposed within a wall of the flexible body 742. The body 742 can be wrapped around the catheter 110, while the inflation chamber(s) 746 are in the deflated position, with the first surface 736 contacting the outer surface of the catheter 110. With the body 742 secured about the catheter 110, the inflation chambers 746 can be inflated to compress the catheter 110 and occlude the catheter lumen 114, transitioning the catheter occlusion system 740 to the closed position, as described herein.

Figure 9A:
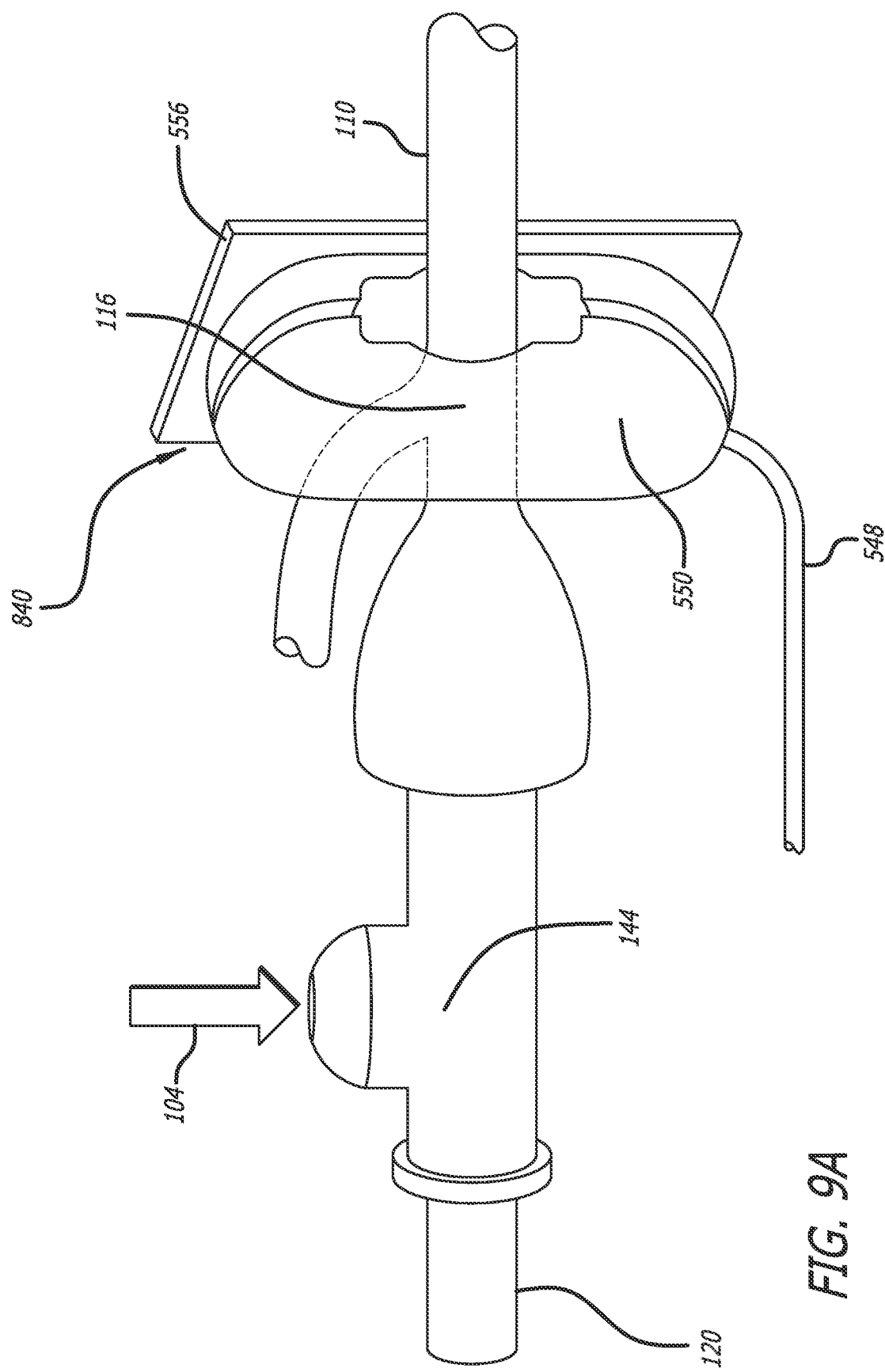
FIG. 9A shows a perspective view of a catheter occlusion system coupled with a catheter, in accordance with embodiments disclosed herein.
Figure 9B:
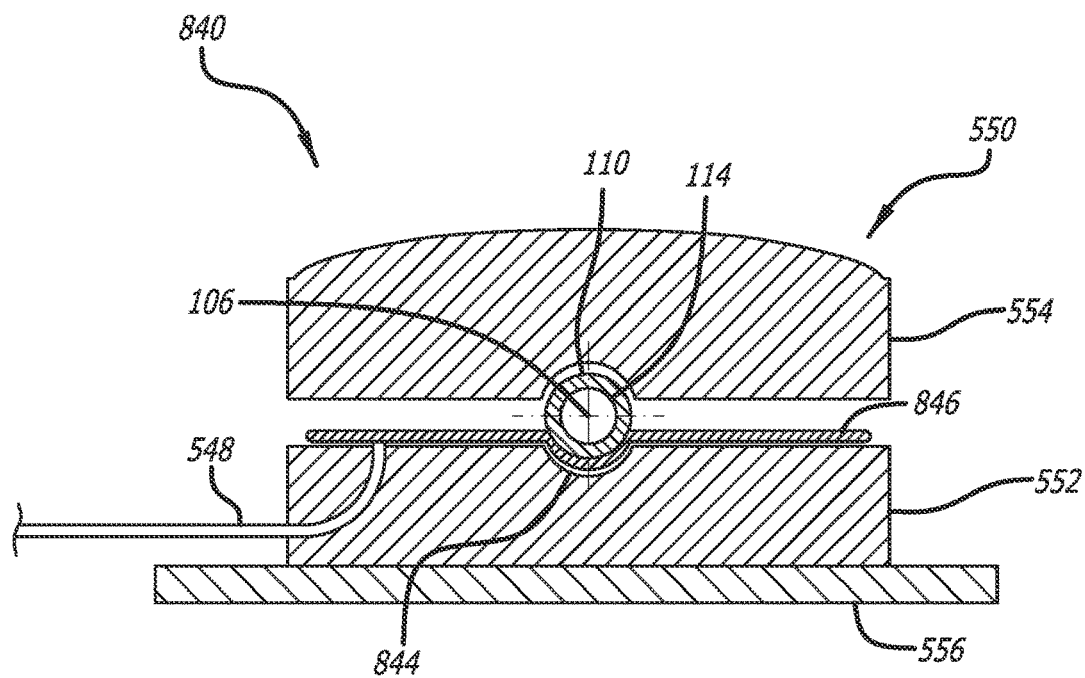
FIG. 9B shows a cross sectional view of a catheter occlusion system coupled with a catheter in a deflated state, in accordance with embodiments disclosed herein.
Figure 9C:
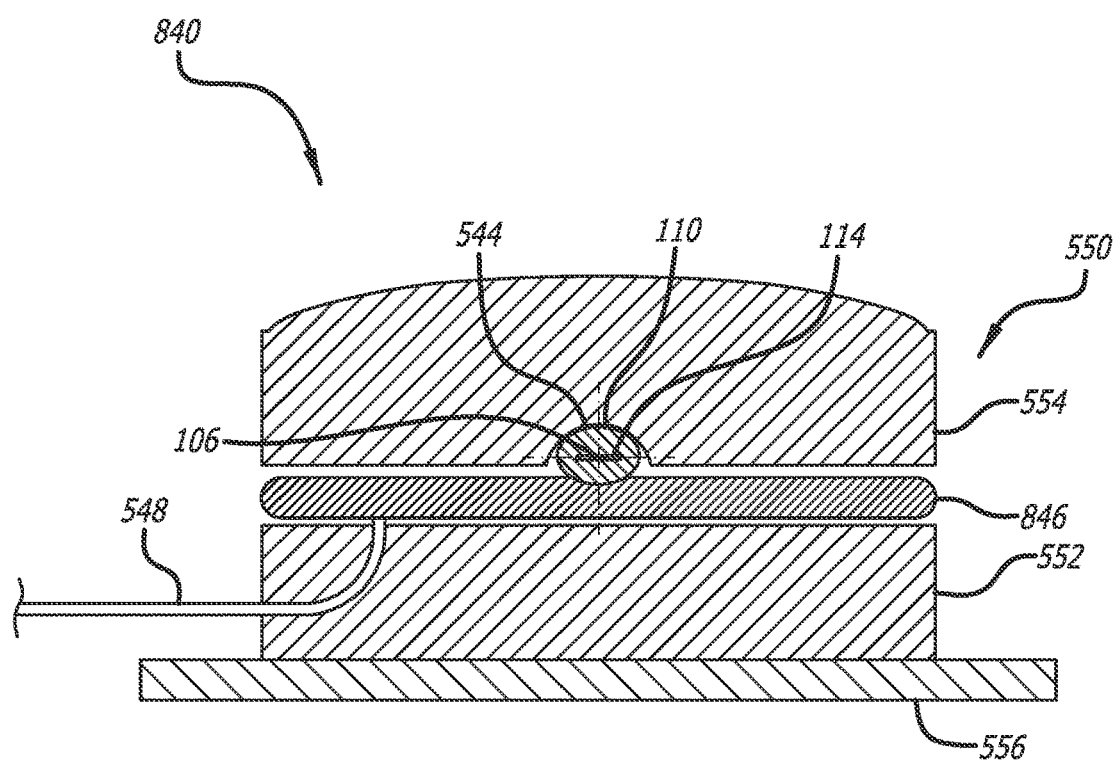
FIG. 9C shows a cross sectional view of a catheter occlusion system coupled with a catheter in an inflated state, in accordance with embodiments disclosed herein.

As shown in FIGS. 9A-9E, in an embodiment, a catheter occlusion system 840 can be integrated with a catheter stabilization device 550. The stabilization device 550 can generally include a body 552, supported by an anchor pad 556, and include a latch 554 or similar structure configured to releasably secure the catheter 110 to the body 552. The anchor pad 556 or a lower surface of the body 552 can include an adhesive layer configured to secure the stabilization device 550 to a skin surface of the patient. One or both of the body 552 and the latch 554 can include a channel 844 extending longitudinally and configured to receive a portion of the catheter 110 therein. The stabilization device 550 can further include an inflation chamber 846 disposed within a surface of one or both of the body 552 or the latch 554. In an embodiment, as shown in FIGS. 9B-9C, the inflation chamber 846 can either be an inflation balloon, as described herein.

Figure 9D:
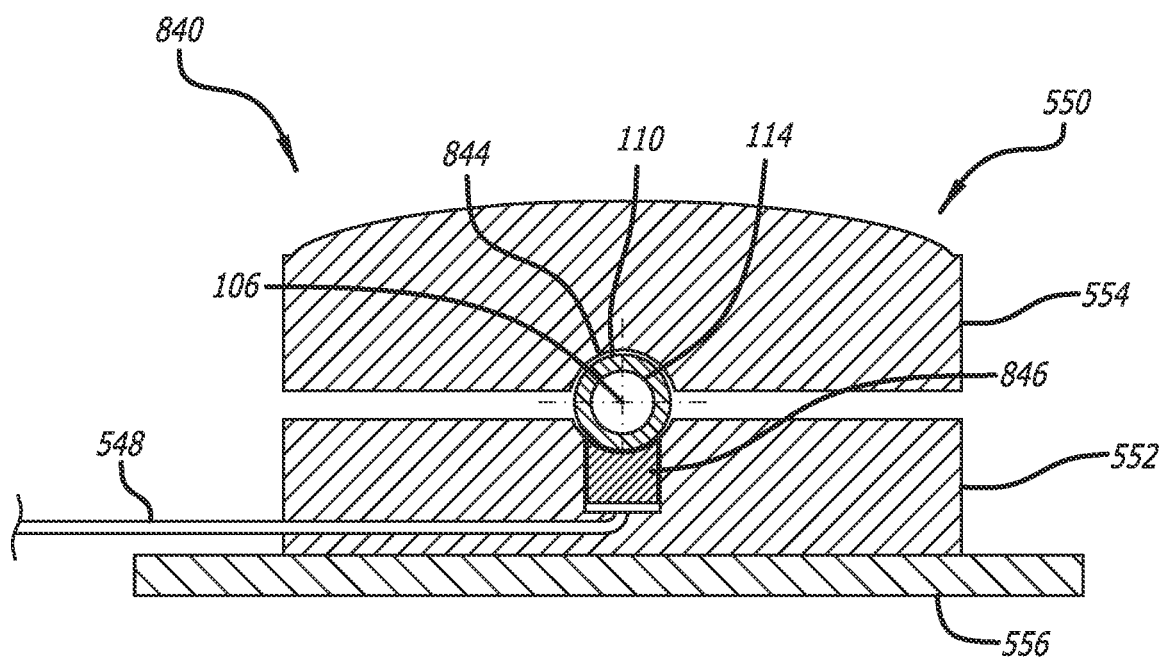
FIG. 9D shows a cross sectional view of a catheter occlusion system coupled with a catheter in a retracted state, in accordance with embodiments disclosed herein.
Figure 9E:
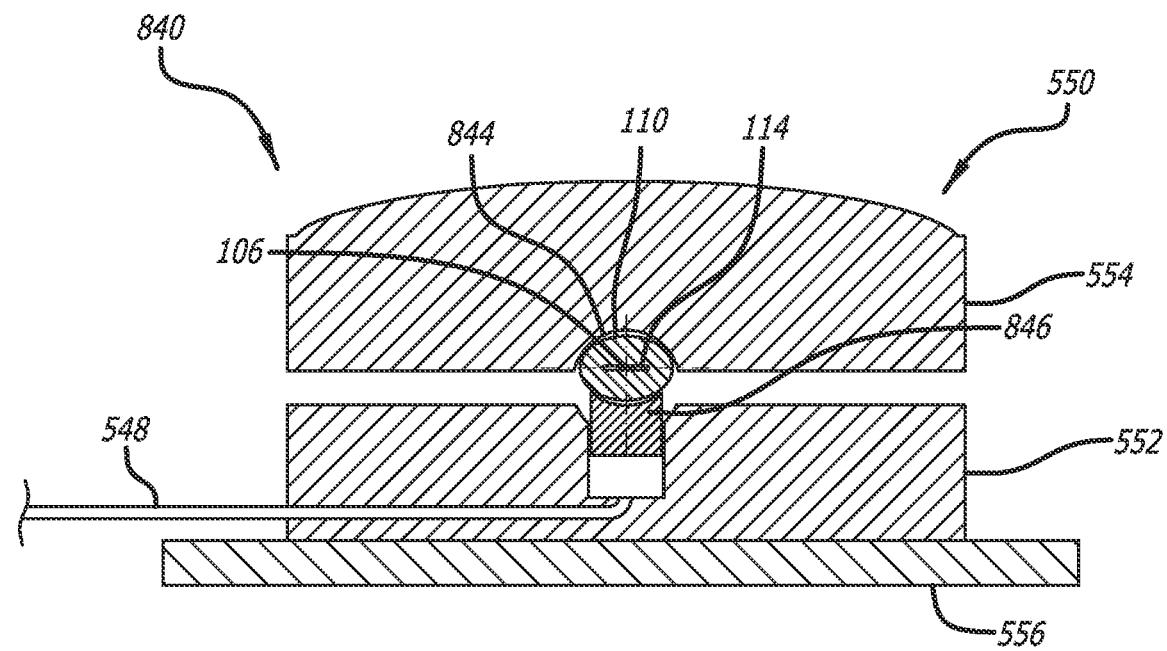
FIG. 9E shows a cross sectional view of a catheter occlusion system coupled with a catheter in an extended state, in accordance with embodiments disclosed herein.

In an embodiment, as shown in FIGS. 9D-9E, the inflation chamber 846 can be a piston chamber including a piston head slidably engaged therewith, as described herein. The inflation chamber 846 can transition between a deflated or retracted state (FIGS. 9B, 9D) and an inflated or extended state (FIGS. 9C, 9E) along an axis extending perpendicular to the longitudinal axis 106 of the catheter 110. With the catheter 110 received within the stabilization device 550, the inflation chamber 846 can be inflated and can compress the catheter 110 against one of the body 552 or the latch 554 to occlude the catheter lumen 114 and transition the catheter occlusion system 840 to the closed state, as described herein. Similarly, the inflation chamber 846 can be actively or passively deflated to transition the catheter occlusion system 840 to the open state, as described herein. Advantageously, embodiments described herein allow for remote or automatic occlusion of the catheter lumen 114. The catheter occlusion device can be included as part of an active clearing system 100 configured to clear dependent loops from a fluid drainage system.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A drainage system for draining a fluid from a patient, the drainage system comprising:
    a drainage tube configured to provide fluid communication between a catheter and a collection container;
    an input airflow device coupled to the drainage tube and configured to provide airflow into the drainage tube;
    a pressure sensor operatively coupled to the drainage tube to measure an internal pressure of the drainage tube;
    an output airflow device coupled to the collection container to draw airflow out of the drainage tube; and
    a controller communicatively coupled to the pressure sensor, the input airflow device, and the output airflow device, the controller including control logic configured to:
        (i) acquire pressure data from the pressure sensor;
        (ii) determine a running pressure rate-of-change from the acquired pressure data;
        (iii) compare the running pressure rate-of-change with a pressure rate-of-change defined by the control logic;
        (iv) adjust an operating characteristic of at least one of the input airflow device and the output airflow device to move the running pressure rate-of-change toward the pressure rate-of-change defined by the control logic; and
        (v) measuring a pressure noise level to determine a presence of droplets within the drainage tube and modifying the input airflow device from a first airflow rate to a second airflow rate by modifying the pressure rate-of-change defined by the control logic.

2. The system according to claim 1, wherein the control logic is configured to adjust the operating characteristic of the output airflow device to move the running pressure rate-of-change toward the pressure rate-of-change defined by the control logic.

3. The system according to claim 1, wherein the control logic is configured to:
    compare the running pressure rate-of-change with a positive pressure rate-of-change limit defined by the control logic; and
    deactivate the input airflow device when the running pressure rate-of-change exceeds the positive pressure rate-of-change limit.

4. The system according to claim 1, wherein the control logic is configured to:
    compare the running pressure rate-of-change with a negative pressure rate-of-change limit defined by the control logic; and
    deactivate the output airflow device when the running pressure rate-of-change exceeds the negative pressure rate-of-change limit.

5. The system according to claim 1, wherein the control logic is configured to:
    determine the internal pressure of the drainage tube from the acquired pressure data;
    compare the internal pressure with a positive pressure limit defined by the control logic; and
    deactivate the input airflow device when the internal pressure exceeds the positive pressure limit defined by the control logic.

6. The system according to claim 5, wherein the control logic is configured to:
    compare the internal pressure with a negative pressure limit defined by the control logic; and
    deactivate the output airflow device when the internal pressure exceeds the negative pressure limit.

7. The system according to claim 1, further comprising a valve coupled in line with the drainage tube at a location distal the input airflow device, wherein the valve is configured to selectively allow fluid flow through the valve when open and prevent fluid flow through the valve when closed.

8. The system according to claim 7, wherein the valve is coupled to the controller, and wherein the control logic is configured to close the valve when at least one of the input airflow device and the output airflow device is activated.

9. The system according to claim 7, wherein the valve includes a catheter occlusion system having a body defining a channel configured to receive a portion of the catheter therein, and a first inflation chamber configured to transition between a deflated state and an inflated state, a portion of the first inflation chamber extending into the channel in the inflated state to compress the catheter and occlude a lumen of the catheter.

10. The system according to claim 9, wherein the first inflation chamber includes one of an expandable balloon or a piston having a piston head slidably engaged therewith.

11. The system according to claim 9, wherein the first inflation chamber extends between the deflated state and the inflated state along an inflation axis that extends perpendicular to a longitudinal axis of the catheter, the inflation axis being offset from a radial mid-point of the lumen of the catheter, disposed between a channel opening and the radial mid-point of the lumen of the catheter.

12. The system according to claim 9, wherein the body encircles the catheter through an arc of 360° and defines a toroidal cross-sectional shape.

13. The system according to claim 9, further including an inflation line coupled to the input airflow device and configured to provide an inflation fluid to the first inflation chamber.

14. The system according to claim 7, further comprising a safety pressure sensor operatively coupled to the drainage tube distal the valve, wherein the safety pressure sensor is coupled to the controller, and wherein the control logic is configured to:
acquire pressure data from the safety pressure sensor;
determine an internal pressure of the catheter from the acquired pressure data from the safety pressure sensor;
compare the internal pressure of the catheter with at least one of a positive pressure limit for the catheter and a predefined negative pressure limit for the catheter; and
deactivate the input airflow device and the output airflow device when the internal pressure of the catheter exceeds a predefined positive pressure limit for the catheter or the predefined negative pressure limit for the catheter.

15. The system according to claim 1, wherein the control logic is configured to:
acquire pressure data from the pressure sensor while the input airflow device is deactivated;
generate one or more pressure parameters from the pressure data;
compare the one or more pressure parameters with one or more corresponding pressure parameter limits defined by the control logic; and
activate the input airflow device when a pressure parameter exceeds at least one of the one or more corresponding pressure parameter limits.

16. The system according to claim 1, wherein the control logic is configured to deactivate the input airflow device after a predefined activation time period defined by the control logic.

17. The system according to claim 1, further comprising a hydrophobic filter coupled in line with the drainage tube between the collection container and the output airflow device.

18. The system according to claim 1, wherein the catheter is a Foley catheter configured to drain the fluid from a bladder of the patient.

19. A method of draining fluid from a patient, comprising:
providing a drainage system comprising:
a drainage tube extending between a catheter and a collection container, wherein the drainage tube, the catheter and the collection container are in fluid communication with each other;
a pressure sensor operatively coupled to the drainage tube to measure pressure within the drainage tube;
an input airflow device coupled to the drainage tube at a distal end to provide airflow into the drainage tube;
a valve coupled in line with the drainage tube between the catheter and the input airflow device, wherein the valve is configured to selectively allow fluid flow through the valve when open and prevent fluid flow through the valve when closed;
an output airflow device coupled to the drainage tube at a proximal end, the output airflow device configured to draw airflow out of the drainage tube; and
a controller including control logic, the controller coupled to the pressure sensor, the input airflow device, the output airflow device, and the valve;
acquiring pressure data from the pressure sensor;
generating one or more pressure parameters from the pressure data, including a pressure rate-of-change, a running pressure rate-of-change, and a pressure noise level;
comparing the one or more pressure parameters with one or more corresponding pressure parameter limits; and
activating the input airflow device when at least one pressure parameter exceeds at least one of the one or more corresponding pressure parameter limits including measuring the pressure noise level to determine a presence of droplets within the drainage tube and modifying the input airflow device from a first airflow rate to a second airflow rate.

* * * * *